US007700759B2

(12) United States Patent
Prasad et al.

(10) Patent No.: US 7,700,759 B2
(45) Date of Patent: Apr. 20, 2010

(54) APTAMER CONSTRUCTS

(75) Inventors: Vinayaka R. Prasad, Yonkers, NY (US); Pheroze Joshi, Bronx, NY (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 1104 days.

(21) Appl. No.: 10/999,686

(22) Filed: Nov. 30, 2004

(65) Prior Publication Data

US 2005/0222400 A1    Oct. 6, 2005

Related U.S. Application Data

(63) Continuation-in-part of application No. PCT/US03/17182, filed on May 29, 2003.

(60) Provisional application No. 60/384,376, filed on May 30, 2002.

(51) Int. Cl.
*C07H 21/04* (2006.01)
(52) U.S. Cl. .................. 536/24.5; 536/24.31; 536/24.1; 435/6; 435/325; 435/375
(58) Field of Classification Search ........................ None
See application file for complete search history.

(56) References Cited

U.S. PATENT DOCUMENTS 5,500,357 A * 3/1996 Taira et al. ............... 435/91.31
6,740,750 B1 * 5/2004 Taira et al. .................. 536/24.5

OTHER PUBLICATIONS

Kensch et al. HIV- Reverse Transcriptase-Pseudoknot RNA Aptamer Interaction Has a Binding Affinity in the Low Picomolar Range Coupled with Hight Specificity. Journal of Biological Chemistry 2000, vol. 275, No. 24. pp. 18271-18278.*
Morgenstern et al. Advanced mammalina gene transfer: high tire retorviral vectors with multiple drug selection markers and a complementary helper-free packing cell line. Nucleic Acids Research 1990, vol. 18, No. 12 pp. 3587-3596.*
Rosenzweig et al. Induction of cytotoxic T lymphocyte and antibody responses to enhanced green fluorescent protein following transplantation of transduced CD34+ hematopoietic cells. Blood 2001, vol. 97, No. 7, pp. 1951-1959.*
Gervaix et al. Gene Therapy Targeting Peripheral Blood CD34+ Hematopoietic Stem Cells of HIV-Infected Individuals. Human Gene Therapy 1997, vol. 8, pp. 2229-2238.*
International Search Report in connection with PCT Patent Application No. PCT/US2003/017182 filed May 29, 2003.
Joshi P et al., entitled Potent Inhibition of Human Immunodeficiency Virus Type 1 Replication by Template Analog Reverse Transcriptase Inhibitors Derived by Selex (Systematic Evolution of Ligands by Exponential Enrichment), Journal of Virology, Jul. 2002, vol. 76, No. 13, 6545-6557.
Nishikawa F et al., entitled "Inhibition of HCV NS3 protease by RNA aptamers in cells," Nucleic Acids Research, 2003, vol. 31, No. 7, 1935-1943.
Benedict C M et al., entitled "Triple ribozyme-mediated down-regulation of the retinoblastoma gene," Carcinogenesis, 1998, vol. 19, No. 7, 1223-1230.
International Preliminary Examination Report in connection with PCT Patent Application No. PCT/US2003/017182 filed May 29, 2003.

* cited by examiner

*Primary Examiner*—Kimberly Chong
(74) *Attorney, Agent, or Firm*—Amster, Rothstein & Ebenstein LLP

(57) ABSTRACT

Provided are RNA oligonucleotides having an aptamer flanked by two self-cleaving ribozymes. Vectors encoding the oligonucleotides, and cells transfected with these vectors are also provided. Additionally, methods of inhibiting replication of a virus in a cell, methods of treating an organism with an aptamer, methods of determining whether a test aptamer is effective in inhibiting the function of a target of the aptamer in a cell, and methods of expressing an RNA aptamer in a cell are provided.

32 Claims, 22 Drawing Sheets

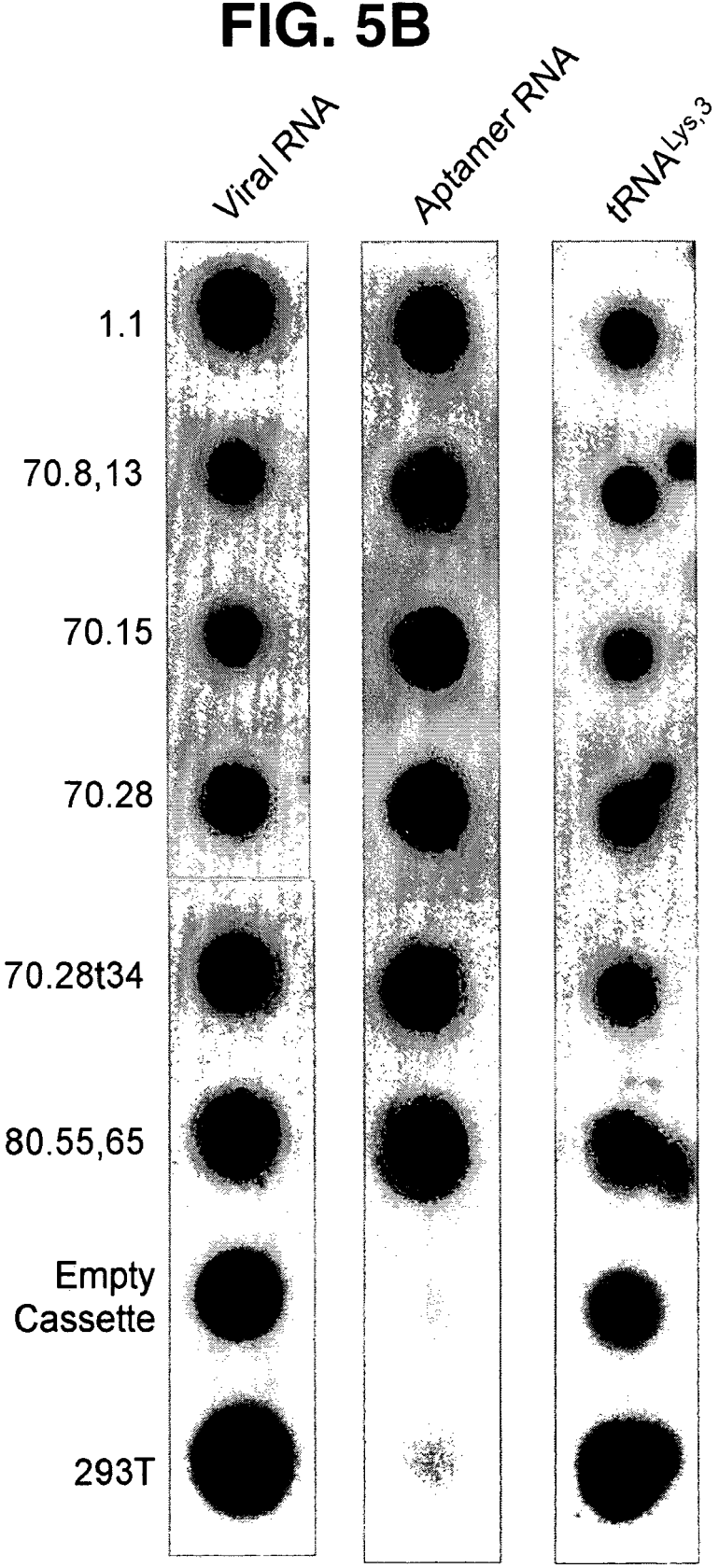

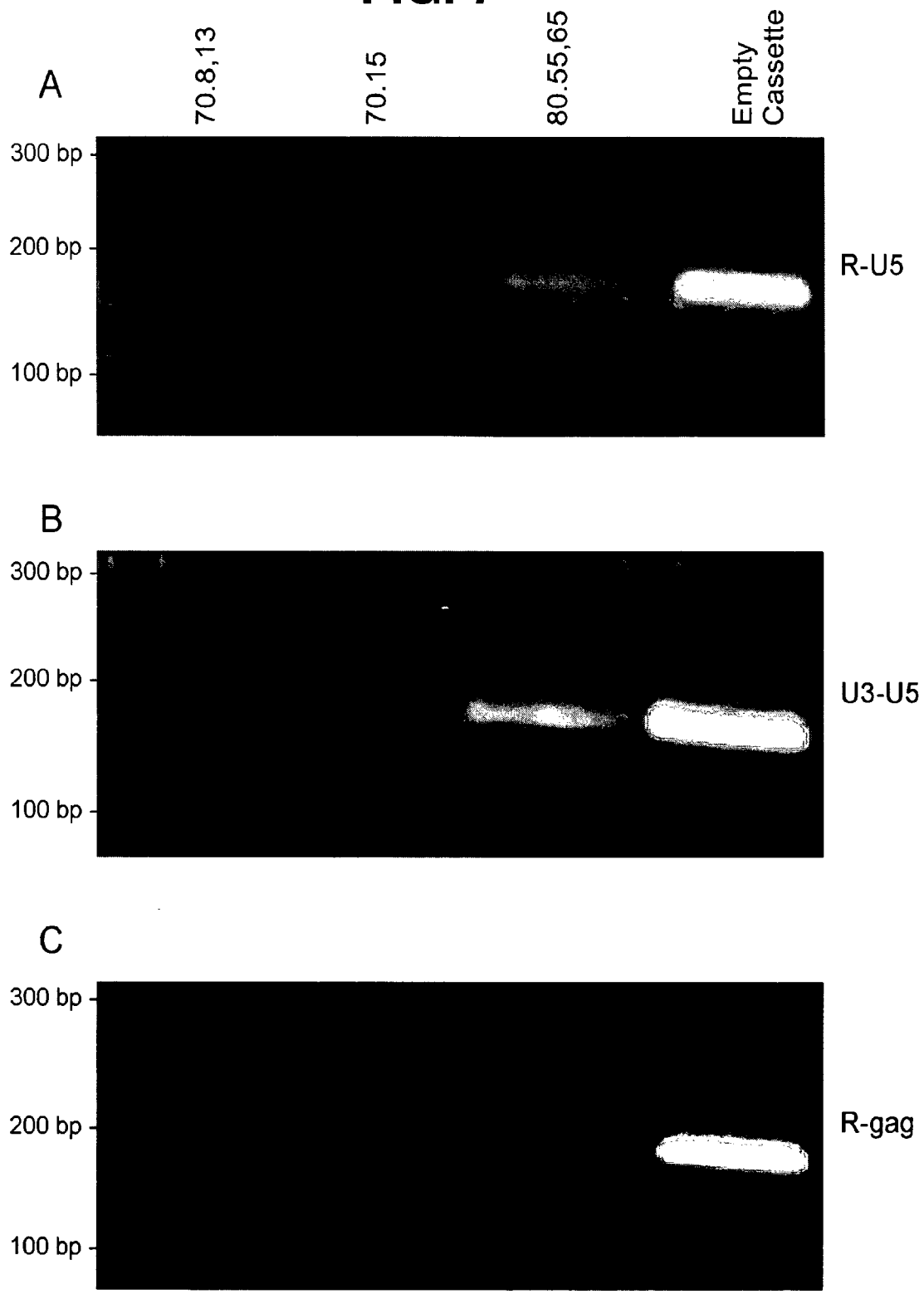

SEQUENCE LISTING

```
<160> NUMBER OF SEQ ID NOS: 15

<210> SEQ ID NO 1
<211> LENGTH: 66
<212> TYPE: DNA
<213> ORGANISM: Artificial
<220> FEATURE:
<223> OTHER INFORMATION: aptamer

<400> SEQUENCE: 1
agctcgagct cgaattcggg agattccgtt ttcagtccgg gaaaaactga agggcccgga    60
tccgtc                                                              66

<210> SEQ ID NO 2
<211> LENGTH: 77
<212> TYPE: DNA
<213> ORGANISM: Artificial
<220> FEATURE:
<223> OTHER INFORMATION: aptamer

<400> SEQUENCE: 2
agctcgagct cgaattcaaa gagatctggc agtgtcacaa ccaggaaaaa gacacgacga    60
acgggcccgg atccgtc                                                  77
```

```
<210> SEQ ID NO 3
<211> LENGTH: 72
<212> TYPE: DNA
<213> ORGANISM: Artificial
<220> FEATURE:
<223> OTHER INFORMATION: aptamer

<400> SEQUENCE: 3
agctcgagct cgaattccct acgaacccag gagataaggg ggaaaactct ggaaaacggg    60
cccggatccg tc                                                       72

<210> SEQ ID NO 4
<211> LENGTH: 77
<212> TYPE: DNA
<213> ORGANISM: Artificial
<220> FEATURE:
<223> OTHER INFORMATION: aptamer

<400> SEQUENCE: 4
agctcgagct cgaattcaca agaaccggac cgggtgagaa ccgagacaaa cacccaccaa    60
gagggcccgg atccgtc                                                  77

<210> SEQ ID NO 5
<211> LENGTH: 66
<212> TYPE: DNA
<213> ORGANISM: Artificial
<220> FEATURE:
<223> OTHER INFORMATION: aptamer

<400> SEQUENCE: 5
agctcgagct cgaattcggg aaccggacgg gtgagaaccg agacaaacac cgggcccgga    60
tccgtc                                                              66

<210> SEQ ID NO 6
<211> LENGTH: 78
<212> TYPE: DNA
<213> ORGANISM: Artificial
<220> FEATURE:
<223> OTHER INFORMATION: aptamer

<400> SEQUENCE: 6
agctcgagct cgaattcatt taattccata atggctcacc acaaggggaa cgttgatgaa    60
atagggcccg gatccgtc                                                 78

<210> SEQ ID NO 7
<211> LENGTH: 17
<212> TYPE: DNA
<213> ORGANISM: Artificial
<220> FEATURE:
<223> OTHER INFORMATION: portion of aptamer

<400> SEQUENCE: 7
agctcgagct cgaattc                                                  17

<210> SEQ ID NO 8
<211> LENGTH: 15
<212> TYPE: DNA
<213> ORGANISM: Artificial
<220> FEATURE:
<223> OTHER INFORMATION: portion of aptamer

<400> SEQUENCE: 8
gggcccggat ccgtc                                                    15
```

<210> SEQ ID NO 9
<211> LENGTH: 35
<212> TYPE: DNA
<213> ORGANISM: Artificial
<220> FEATURE:
<223> OTHER INFORMATION: primer

<400> SEQUENCE: 9
aattaaccct cactaaaggg tagacaattc actgc                    35

<210> SEQ ID NO 10
<211> LENGTH: 22
<212> TYPE: DNA
<213> ORGANISM: Artificial
<220> FEATURE:
<223> OTHER INFORMATION: primer

<400> SEQUENCE: 10
gcatgcctgc tattgtcttc cc                                  22

<210> SEQ ID NO 11
<211> LENGTH: 186
<212> TYPE: RNA
<213> ORGANISM: Artificial
<220> FEATURE:
<223> OTHER INFORMATION: ribozyme-aptamer-ribozyme

<400> SEQUENCE: 11
gcuggcuagc ucgagcucug augaguccgu gaggacaaac gguacccggu accgucagcu    60
cgagcucgaa uuccaagaac cggacgggug agaaccgaga caaacaccca caagggcccg   120
gauccgucga cggaucuaga uccguccuga ugaguccgug aggacaaacg gaucugcagc   180
ggccgc                                                             186

<210> SEQ ID NO 12
<211> LENGTH: 163
<212> TYPE: RNA
<213> ORGANISM: Artificial
<220> FEATURE:
<223> OTHER INFORMATION: tRNAVal promoter / 5' Ribozyme

<400> SEQUENCE: 12
accguagguu uccguagugu agugguuauc acguucggcc uaacacgccg aaaggucccc    60
gguucgaaac cgggcacuac aaaaaccaac gcuggcuagc ucgagcucug augaguccgu   120
gaggacaaac gguacccggu accgucagcu cgagcucgaa uuc                    163

<210> SEQ ID NO 13
<211> LENGTH: 76
<212> TYPE: RNA
<213> ORGANISM: Artificial
<220> FEATURE:
<223> OTHER INFORMATION: 3' Ribozyme / terminator

<400> SEQUENCE: 13
gggcccggau ccgucgacgg aucuagaucc guccugauga guccgugagg acaaacggau    60
cugcagcggc cgcuuu                                                   76

<210> SEQ ID NO 14
<211> LENGTH: 6
<212> TYPE: RNA
<213> ORGANISM: Artificial
<220> FEATURE:

```
-continued

<223> OTHER INFORMATION: 5' connector sequence

<400> SEQUENCE: 14 gucuag                                                                                6

<210> SEQ ID NO 15
<211> LENGTH: 29
<212> TYPE: RNA
<213> ORGANISM: Artificial
<220> FEATURE:
<223> OTHER INFORMATION: 3' connector sequence

<400> SEQUENCE: 15
gcccggauga gcggacgcuu guccgcuuu                                                      29
```

APTAMER CONSTRUCTS

CROSS-REFERENCE TO RELATED APPLICATION

This is a continuation-in-part of International Application PCT/US03/17182, with an international filing date of May 29, 2003, which claims the benefit of U.S. Provisional Application No. 60/384,376, filed May 30, 2002.

STATEMENT REGARDING FEDERALLY FUNDED RESEARCH OR DEVELOPMENT

The U.S. Government has a paid-up license in this invention and the right in limited circumstances to require the patent owner to license others on reasonable terms as provided by the terms of Grant No. AI061797 awarded by the National Institutes of Health.

BACKGROUND (1) Field of the Invention

The present invention generally relates to aptamers. More specifically, the invention relates to aptamers that can be expressed in cells.

(2) Description of the Related Art

REFERENCES CITED

Bai, J., J. Rossi, and R. Akkina 2001. Multivalent anti-CCR ribozymes for stem cell-based HIV type I gene therapy. AIDS Res Hum Retroviruses 17:385-99.

Balzarini, J., De Clercq, E., Uberla, K. 1997. SIV/HIV-1 hybrid virus expressing the reverse transcriptase gene of HIV-1 remains sensitive to HIV-1-specific reverse transcriptase inhibitors after passage in rhesus macaques. J Acquir immune Defic Syndr Hum Retrovirol. 15:1-4.

Benedict, C. M., W. Pan, S. E. Loy, and G. A. Clawson 1998. Triple ribozyme-mediated down-regulation of the retinoblastoma gene. Carcinogenesis 19:1223-30.

Boden, D. et al. 2003. Promoter choice affects the potency of HIV-1 specific RNA interference. Nucleic Acids Res 31:5033-8.

Bridges, S. H., and N. Sarver 1995. Gene therapy and immune restoration for HIV disease. Lancet 345:427-32.

Brinkmann, K., A. Smeitink, A. Romijn, and P. Rieiss 1999. Mitochondrial toxicity induced by nucleoside-analog reverse transcriptase inhibitors is a key factor in the pathogenesis of anti-retroviral therapy-related lipodystrophy. Lancet 354:1112-1115.

Bukrinsky, M. I. et al. 1993. Association of integrase, matrix, and reverse transcriptase antigens of human immunodeficiency virus type 1 with viral nucleic acids following acute infection. Proc Natl Acad Sci USA 90:6125-9.

Butler, S. L., Hansen, M. S. & Bushman, F. D. 2001. A quantitative assay for HIV DNA integration in vivo. Nat Med 7:631-4.

Burke, D. H., L. Scates, K. Andrews, and L. Gold 1996. Bent pseudoknots and novel RNA inhibitors of type 1 human immunodeficiency virus (HIV-1) reverse transcriptase. J. Mol. Biol. 264:650-666.

Cann, J. R. 1996. Theory and practice of gel electrophoresis of interacting macromolecules. Anal. Biochem. 237:1-16.

Castanotto, D., Li, H. & Rossi, J. J. 2002. Functional siRNA expression from transfected PCR products. RNA 8:1454-60.

Charneau, P., G. Mirambeau, P. Roux, S. Paulous, H. Buc, and F. Clavel 1994. HIV-1 reverse transcription: A termination step at the center of the genome. J. Mol. Biol. 241:651-662.

Coburn, G. A. & Cullen, B. R. 2002. Potent and specific inhibition of human immunodeficiency virus type 1 replication by RNA interference. J Virol 76:9225-331.

Das, A. T. et al. 2004. Human immunodeficiency virus type I escapes from RNA interference-mediated inhibition. J Virol 78:2601-5.

Dirani-Diab, R. E., L. Sarih-Cottin, B. Delord, B. Dumon, S. Moreau, J.-J. Toulme, H. Fleury, and S. Litwak 1997. Phosphorothioate oligonucleotides derived from human immunodeficiency virus type 1 (HIV-1) primer tRNA$^{Lys3}$ are strong inhibitors of HIV-1 reverse transcriptase and arrest iral replication in infected cells. Antimicrob. Agents Chemother. 41:2141-2148.

Ellington, A. D., and J. W. Szostak 1990. In vitro selection of RNA molecules that bind specific ligands Nature 346:818-22.

Fassati, A. & Goff, S. P. 2001. Characterization of intracellular reverse transcription complexes of human immunodeficiency virus type 1. J Virol 75:3626-35.

Fisher, T. S., P. J. Joshi, and V. R. Prasad 2002. Mutations that confer resistance to template analog inhibitors of human immunodeficiency virus type 1 (HIV-1) reverse transcriptase lead to severe defects in HIV replication. J. Virol. 76:4068-4072.

Giuffre, A. C., Higgins, J., Buckheit, R. W., Jr. & North, T. W. 2003. Susceptibilities of simian immunodeficiency virus to protease inhibitors. Antimicrob Agents Chemother 47:1756-9.

Hannon, G. J. & Rossi, J. J. 2004. Unlocking the potential of the human genome with RNA interference. Nature 431:371-8.

Hirao, I., M. Spingola, D. Peabody, and A. D. Ellington 1998. The limits of specificity: an experimental analysis with RNA aptamers to MS2 coat protein variants. Mol Divers. 4:75-89.

Hu, W. Y., Bushman, F. D. & Siva, A. C. 2004. RNA interference against retroviruses. Virus Res 102:59-64.

Jacque, J. M., Triques, K. & Stevenson, M. 2002. Modulation of HIV-1 replication by RNA interference. Nature 418:435-8.

Jaeger, J., T. Restle, and T. A. Steitz 1998. The Structure of HIV-1 Reverse Transcriptase Complexed with an RNA Pseudoknot Inhibitor. The EMBO Journal 17:4535.

Jayan, G. C., P. Cordelier, C. Patel, M. BouHamdan, R. P. Johnson, J. Lisziewicz, R. J. Pomerantz, and D. S. Strayer 2001. SV40-derived vectors provide effective transgene expression and inhibition of HIV-1 using constitutive, conditional, and pol III promoters. Gene Ther. 8:1033-42.

Joshi, P. and Prasad, V. R. 2002. Potent inhibition of human immunodeficiency virus type I replication by template analog reverse transcriptase inhibitors derived by SELEX (systematic evolution of ligands by exponential enrichment). J. Virol. 76:6545-57.

Joshi, P. J., Fisher, T. S. & Prasad, V. R 2003. Anti-HIV inhibitors based on nucleic acids: emergence of aptamers as potent antivirals. Curr Drug Targets Infect Disord 3:383-400.

Julias, J. G., Ferris, A. L., Boyer, P. L. & Hughes, S. H. 2001. Replication of phenotypically mixed human immunodeficiency virus type 1 virions containing catalytically active and catalytically inactive reverse transcriptase. J Virol 75:6537-46.

Kato, Y., Kuwabara, T., Warashina, M., Toda, H., Taira, K. 2001. Relationships between the activities in vitro and in vivo of various kinds of ribozyme and their intracellular localization in mammalian cells. J Biol. Chem. 276:15378-85

Kawasaki, H. & Taira, K. 2003. Short hairpin type of dsRNAs that are controlled by tRNA(Val) promoter significantly induce RNAi-mediated gene silencing in the cytoplasm of human cells. Nucleic Acids Res 31:700-7.

Kensch, O., B. A. Connolly, H. J. Steinhoff, A. McGregor, R. S. Goody, and T. Restle 2000. HIV-1 reverse transcriptase-pseudoknot RNA aptamer interaction has a binding affinity in the low picomolar range coupled with high specificity. J Biol Chem. 275:18271-8.

Konopka, K., N. Duzgunes, J. Rossi, and N. S. Lee 1998. Receptor ligand-facilitated cationic liposome delivery of anti-HIV-1 Rev binding aptamer and ribozyme DNAs. J. Drug Target. 5:247-259.

Lee, N. S. & Rossi, J. J. 2004. Control of HIV-1 replication by RNA interference. Virus Res 102:53-8.

Lee, R., N. Kaushik, M. J. Modak, R. Vinayak, and V. N. Pandey 1998. Polyamide nucleic acid targeted to the primer binding site of the HIV-1 RNA genome blocks in vitro HIV-1 reverse transcription. Biochemistry 37:900-10.

Lee, S. W., H. F. Gallardo, E. Gilboa, and C. Smith 1994. Inhibition of human immunodeficiency virus type 1 in human T cells by a potent Rev response element decoy consisting of the 13-nucleotide minimal Rev-binding domain. J. Virol. 68:8254-64.

Lee, N. S. et al. 2002. Expression of small interfering RNAs targeted against HIV-1 rev transcripts in human cells. Nat Biotechnol 20:500-5.

Li, M. J. et al. 2003. Inhibition of HIV-1 infection by lentiviral vectors expressing Pol III-promoted anti-HIV RNAs. Mol Ther 8:196-206.

Lu, Y., V. Planelles, X. Li, C. Palaniappan, B. Day, P. Challita-Eid, R. Amado, D. Stephens, D. B. Kohn, A. Bakker, P. Fay, R. A. Bambara, and J. D. Rosenblatt 1997. Inhibition of HIV-1 replication using a mutated tRNALys-3 primer. J Biol Chem. 272:14523-31.

Mak, J., M. Jiang, M. A. Wainberg, M. L. Hammarskjold, D. Rekosh, and L. Kleiman 1994. Role of Pr160gag-pol in mediating the selective incorporation of tRNA(Lys) into human immunodeficiency virus type I particles. J. Virol. 68:2065-72.

Mak, J., A. Khorchid, Q. Cao, Y. Huang, I. Lowy, M. A. Parniak, V. R. Prasad, M. A. Wainberg, and L. Kleiman 1997. Effects of mutations in Pr160gag-pol upon tRNA (Lys3) and Pr160gag-plo incorporation into HIV-1 J. Mol. Biol. 265:419-31.

Michienzi, A., L. Cagnon, I. Bahner, and J. J. Rossi 2000. Ribozyme-mediated inhibition of HIV 1 suggests nucleolar trafficking of HIV-1 RNA. Proc Natl Acad Sci USA 97:8955-60.

Mori, K., Y. Yasutomi, S. Sawada, F. Villinger, K. Sugama, B. Rosenwith, J. L. Heeney, K. Uberla, S. Yamazaki, A. A. Ansari, and H. Rubsamen-Waigmann 2000. Suppression of acute viremia by short-term postexposure prophylaxis of simian/human immunodeficiency virus SHIV-RT-infected monkeys with a novel reverse transcriptase inhibitor (GW420867) allows for development of potent antiviral immune responses resulting in efficient containment of infection. J Virol. 74:5747-53.

Murry, J. P. et al. 2003. Reversion of the M 184V mutation in simian immunodeficiency virus reverse transcriptase is selected by tenofovir, even in the presence of lamivudine. J Virol 77:1120-30.

Novina, C. D. et al. 2002. siRNA-directed inhibition of HIV-1 infection. Nat Med 8:681-6.

Paul, C. P. et al. 2003. Localized expression of small RNA inhibitors in human cells. Mol Ther 7:237-47.

Ranga, U., C. Woffendin, S. Verma, L. Xu, C. H. June, D. K. Bishop, and G. J. Nabel 1998. Enhanced T cell engraftment after retroviral delivery of an antiviral gene in HIV-infected individuals. Proc Natl Acad Sci USA 95:1201-6.

Richman, D. D. 2001. HIV Chemothrapy Nature 410:995-1001.

Riviere, I., Brose, K. & Mulligan, R. C. 1995. Effects of retroviral vector design on expression of human adenosine deaminase in murine bone marrow transplant recipients engrafted with genetically modified cells. Proc Natl Acad Sci USA 92:6733-7.

Roos, J. W., M. F. Maughan, Z. Liao, J. E. Hildreth, and J. E. Clements 2000. LuSIV cells: a reporter cell line for the detection and quantitation of a single cycle of HIV and SIV replication. Virology 273:307-15.

Rosenwirth, B., ten Haaft, P., Bogers, W. M., Nieuwenhuis, I. G., Niphuis, H., Kuhn, E. M., Bischofberger, N., Heeney, J. L., Uberla, K. 2000. Antiretroviral therapy during primary immunodeficiency virus infection can induce persistent suppression of virus load and protection from heterologous challenge in rhesus macaques. J Virol. 74:1704-11

Rosenzweig, M. et al. 2001. Induction of cytotoxic T lymphocyte and antibody responses to enhanced green fluorescent protein following transplantation of transduced CD34(+) hematopoietic cells. Blood 97:1951-9.

Schneider, D. J., J. Feigon, Z. Hostomsky, and L. Gold 1995. High-affinity ssDNA inhibitors of the reverse transcriptase of type 1 human immunodeficiency virus. Biochemistry 34:9599-9610.

Soderberg, K. et al. 2002. A nucleotide substitution in the tRNA(Lys) primer binding site dramatically increases replication of recombinant simian immunodeficiency virus containing a human immunodeficiency virus type 1 reverse transcriptase. J Virol 76:5803-6.

Stevenson, M. 2003. Dissecting HIV-1 through RNA interference. Nat Rev Immunol 3:851-8.

Sullenger, B. A., H. F. Gallardo, G. E. Ungers, and E. Gilboa 1990. Overexpression of TAR sequences renders cells resistant to human immunodeficiency virus replication. Cell 63:601-8.

Surabhi, R. M. & Gaynor, R. B. 2002. RNA interference directed against viral and cellular targets inhibits human immunodeficiency Virus Type 1 replication. J Virol 76:12963-73.

Symensma, T. L., S. Baskerville, A. Yan, and A. D. Ellington 1999. Polyvalent Rev decoys act as artificial Rev-responsive elements. J. Virol. 73:4341-9.

Tantillo, C., J. Ding, A. Jacobo-Molina, R. G. Nanni, P. L. Boyer, S. H. Hughes, R. Pauwels, K. Andries, P. A. Janssen, and E. Arnold 1994. Locations of anti-AIDS drug binding sites and resistance mutations in the three-dimensional structure of HIV-1 reverse transcriptase. Implications for mechanisms of drug inhibition and resistance. J. Mol. Biol. 243:369-87.

Tuerk, C., and L. Gold 1992. RNA pseudoknots that inhibit HIV-1 reverse transcriptase Proc. Natl. Acad. Sci. USA 89:6988-6992.

Tuerk, C., and L. Gold 1990. Systematic evolution of ligands by exponential enrichment: RNA ligands to bacteriophage T4 DNA polymerase. Science 249:505-10.

Uberla, K., Stahl-Hennig, C., Bottiger, D., Matz-Rensing, K., Kaup, F. J., Li, J., Haseltine, W. A., Fleckenstein, B., Hunsmann, G., Oberg, B. et al. 1995. Animal model for the therapy of acquired immunodeficiency syndrome with reverse transcriptase inhibitors. Proc Natl Acad Sci USA. 92:8210-4

Wainberg, and L. Kleiman 1997. Effects of mutations in Pr160gag-pol upon tRNA(Lys3) and Pr160gag-plo incorporation into HIV-1. J. Mol. Biol. 265:419-31.

Westaway, S. K., G. P. Larson, S. Li, J. A. Zaia, and J. J. Rossi 1995. A chimeric tRNA(Lys3)-ribozyme inhibits HIV replication following virion assembly. Nucleic Acids Symp Ser. 33:194-9.

Woffendin, C., U. Ranga, Z. Yang, L. Xu, and G. J. Nabel 1996. Expression of a protective gene-prolongs survival of T cells in human immunodeficiency virus-infected patients. Proc Natl Acad Sci USA. 93:2889-94.

Zack, J. A., S. A. Arrigo, S. R. Weitsman, A. S. Go, A. Haislip, and I. S. Y. Chen 1990. HIV-1 entry into quiescent primary lymphocytes: Molecular analysis reveals a labile, latent viral structure. Cell 61:213-222.

U.S. Pat. No. 5,496,938.
U.S. Pat. No. 5,580,737.
U.S. Pat. No. 5,654,151.
U.S. Pat. No. 5,726,017.
U.S. Pat. No. 5,786,462.
U.S. Pat. No. 5,503,978.
U.S. Pat. No. 6,028,186.
U.S. Pat. No. 6,110,900.
U.S. Pat. No. 6,124,449.
U.S. Pat. No. 6,127,119.
U.S. Pat. No. 6,140,490.
U.S. Pat. No. 6,147,204.
U.S. Pat. No. 6,168,778.
U.S. Pat. No. 6,171,795.
U.S. Pat. No. 5,472,841.
U.S. Pat. No. 5,503,978.
U.S. Pat. No. 5,567,588.
U.S. Pat. No. 5,582,981.
U.S. Pat. No. 5,637,459.
U.S. Pat. No. 5,683,867.
U.S. Pat. No. 5,705,337.
U.S. Pat. No. 5,712,375.
U.S. Pat. No. 6,083,696.

Aptamers are single stranded oligonucleotides or oligonucleotide analogs that bind to a particular target molecule, such as a protein or a small molecule (e.g., a steroid or a drug, etc.). Thus, aptamers are the oligonucleotide analogy to antibodies. However, aptamers are smaller than antibodies, generally in the range of 50-100 nt. Their binding is highly dependent on the secondary structure formed by the aptamer oligonucleotide. Both RNA and single stranded DNA (or analog), aptamers are known. See, e.g., Burke et al., 1996; Ellington and Szostak 1990; Hirao et al., 1998; Jaeger et al., 1998; Kensch et al, 2000; Schneider et al., 1995; and U.S. Pat. Nos. 5,773,598; 5,496,938; 5,580,737; 5,654,151; 5,726,017; 5,786,462; 5,503,978; 6,028,186; 6,110,900; 6,124,449; 6,127,119; 6,140,490; 6,147,204; 6,168,778; and 6,171,795.

Aptamers that bind to virtually any particular target can be selected by using an iterative process called SELEX, which stands for Systematic Evolution of Ligands by EXponential enrichment (Burke et al., 1996; Ellington and Szostak, 1990; Schneider et al., 1995; Tuerk and Gold, 1992; Tuerk and Gold, 1990). Several variations of SELEX have been developed which improve the process and allow its use under particular circumstances. See, e.g., U.S. Pat. Nos. 5,472,841; 5,503,978; 5,567,588; 5,582,981; 5,637,459; 5,683,867; 5,705,337; 5,712,375; and 6,083,696.

Most aptamers currently under development are directed to extracellular targets. Examples include growth factors, virus components, cell surface markers, extracellular enzymes, clotting factors, and immune compounds such as complement proteins. These targets are selected because it is difficult to deliver highly charged nucleic acids into the cell, although there has been some success with liposomes. See, e.g., Konopka et al., 1998. Furthermore, aptamers to date are not useful as gene therapy agents because transcribed RNA aptamers generally contain flanking sequences that cause misfolding and thus are believed to interfere with aptamer-target binding.

Thus, there is a need for methods and compositions useful for expressing functional aptamers in cells. Such methods and compositions would avoid the problems associated with delivering the aptamer into the cell. They would also be useful by providing for continual or inducible production of the aptamer. The present invention satisfies that need.

SUMMARY OF THE INVENTION

The inventors have succeeded in developing nucleotide constructs that allow functional aptamers to be expressed in cells. This allows the use of aptamers in cell transfection and gene therapy efforts and circumvents problems in achieving cell entry using exogenously applied aptamers. By enabling expression of aptamers through transfection (including recombinant viral vector-based delivery) of aptamer-encoding constructs, the additional advantage of providing for continuous or inducible production of the aptamers in the transfected cells is achieved.

Accordingly, in some embodiments, the present invention is directed to RNA oligonucleotides comprising an aptamer flanked by two self-cleaving ribozymes.

In other embodiments, the invention is directed to vectors encoding the above oligonucleotides, and cells transfected with these vectors.

The invention is also directed to methods of inhibiting replication of a virus in a cell. The methods comprise transfecting the cell with a vector encoding an oligonucleotide that comprises an aptamer flanked by two self-cleaving ribozymes.

In additional embodiments, the invention is directed to methods of treating an organism with an aptamer. The methods comprise transfecting a cell of the organism with a vector encoding an oligonucleotide that comprises an aptamer flanked by two self-cleaving ribozymes.

Additionally, the invention is directed to methods of determining whether a test aptamer is effective in inhibiting the function of a target of the aptamer in a cell. The methods comprise transfecting the cell with a vector encoding an oligonucleotide that comprises the test aptamer flanked by two self-cleaving ribozymes, and determining whether the function of the target of the aptamer is inhibited in the cell.

The invention is additionally directed to an RNA aptamer produced in a cell, wherein the aptamer is capable of binding to a target molecule, and wherein the aptamer ia not covalently linked to a flanking sequence that interferes with the binding.

In other embodiments, the invention is directed to methods of expressing an RNA aptamer in a cell. The methods comprise transfecting the cell with a vector encoding an oligonucleotide that comprises an aptamer flanked by two self-cleaving ribozymes.

BRIEF DESCRIPTION OF THE DRAWINGS

FIG. 7 are photographs of agarose gels showing the products of PCR using reverse transcription stage specific primers with infected Jurkat T cell DNA as template. Primers used were specific for: Panel A—minus strong stop DNA (R-U5); Panel B—an intermediate formed after the minus strand transfer (U3-R); Panel C—the full-length proviral DNA (R-gag).

DETAILED DESCRIPTION OF THE INVENTION

Figure 1:
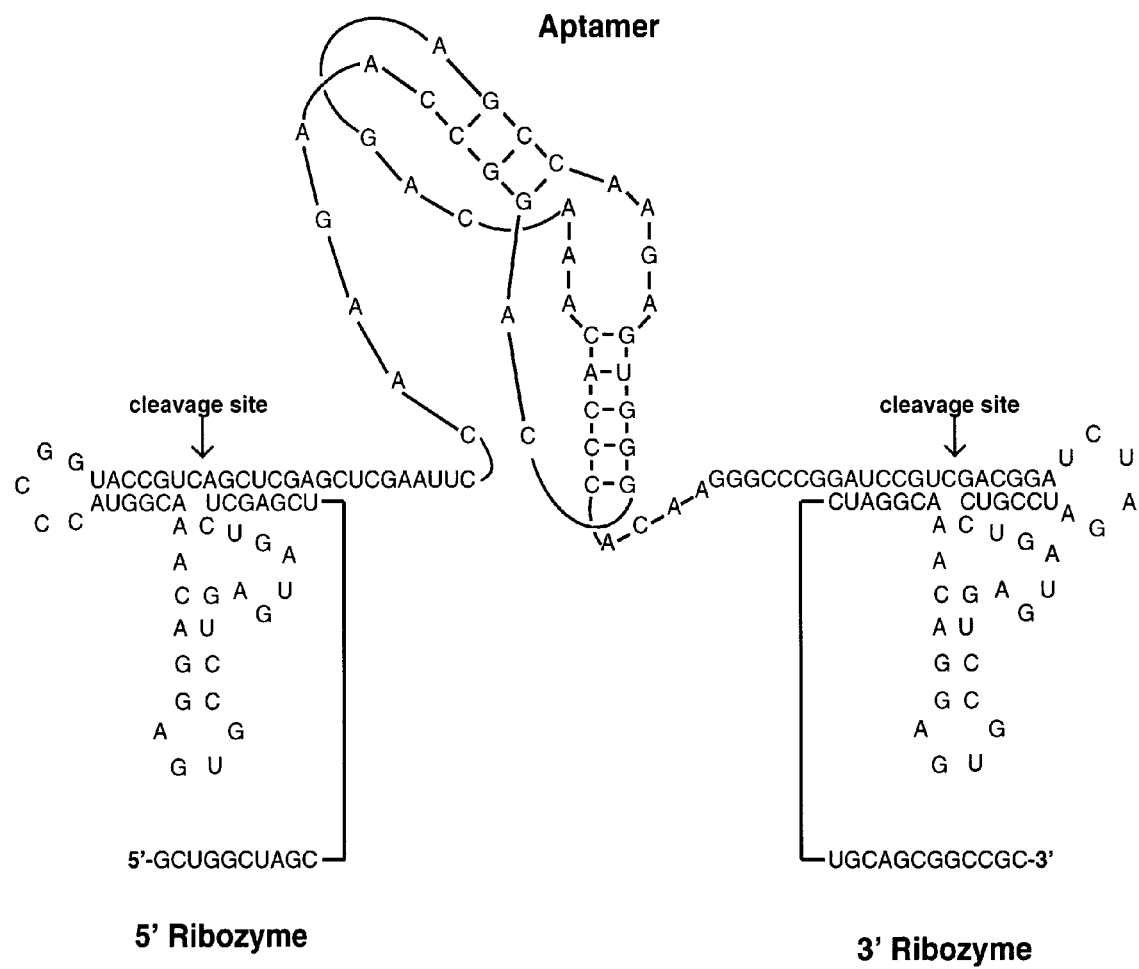
FIG. 1 is a schematic diagram of a representative anti-reverse transcriptase aptamer, 70.28 (SEQ ID NO:4), flanked by self-cleaving ribozymes. The aptamer is represented as a pseudoknot to reflect the secondary structure proposed by Burke et al. (1996). The ribozyme sequences are positioned to cleave the required sites according to Benedict et al. (1998). The sites of cleavage are indicated with arrows. Sequence recited in Figure=SEQ ID NO:11.

The present invention is directed to methods and compositions that allow functional aptamers to be expressed in cells. According to the invention, the aptamers can function after expression in cells by using vectors that encode an RNA oligonucleotide that comprises the aptamer such that the aptamer can be expressed without flanking sequences that can substantially interfere with the aptamer function. In preferred embodiments, this is achieved with an RNA oligonucleotide that comprises the aptamer flanked by two self-cleaving ribozymes. As demonstrated in the Examples, when the oligonucleotide is expressed, the aptamer is released upon cleavage of the self-cleaving ribozymes, and the aptamer that is released has short flanking sequences that are remnants of the self-cleaving ribozymes, which are highly unlikely to interfere with the proper folding of the aptamer sequence, as opposed to prior art methodologies. Without being limited to any particular mechanism, it is believed that these short flanking sequences do not substantially interfere with the aptamer function. The experimental data in Example 1 supports this assertion.

Accordingly, in some embodiments, the invention is directed to an RNA oligonucleotide comprising an aptamer flanked by two self-cleaving ribozymes. The use of the term oligonucleotide does not connote a limitation on its length, and the RNA oligonucleotide can be any length that allows the function of the two self-cleaving ribozymes to release the aptamer. Since it is envisioned that the RNA oligonucleotide is, in preferred embodiments, a transcript from a DNA template, the RNA oligonucleotide can be any length that can be produced by transcription. Other elements, such as additional aptamers, ribozymes, coding regions, leader sequences, etc., can also be part of the RNA oligonucleotide, provided those elements do not substantially interfere with the function of the aptamer or the self-cleaving ribozymes.

As used herein, the term RNA oligonucleotides includes the intact aptamer flanked by two self-cleaving ribozymes, as well as the aptamer and the remnants of the already-cleaved self-cleaving ribozymes. Thus, the RNA oligonucleotide can be in two or more pieces by virtue of the action of the functional self-cleaving ribozymes. Where the RNA oligonucleotide is transcribed from a DNA template (e.g., that is part of a vector introduced into a cell), there needn't ever have been an intact RNA oligonucleotide, since the self-cleaving ribozyme(s) could cleave itself before the entire RNA oligonucleotide is transcribed.

The aptamer in the oligonucleotide can be any useful aptamer now known or later developed. Since the aptamer that is part of the RNA oligonucleotide is preferably expressed inside a viable cell, the aptamer preferably is targeted to a target that is inside a cell. One type of such a target is a component (i.e., a native constituent) of the cell. Any cellular component that could be usefully affected by aptamer binding is envisioned as a potential target of the aptamers of the present invention. Non-limiting examples of such cellular components include proteins such as enzymes, structural proteins, ion channel proteins, electron transport proteins, ribozyme components, lipoproteins and transcription factors; proteoglycans; glycoproteins; polysaccharides; nucleic acids; lipids; and small molecules such as steroids.

Another type of intracellular target for the aptamers of the present invention are deleterious compounds that are not components of the cell. Examples include environmental toxins such as aflatoxin or anthrax toxin, and components of bacteria, fungi or viruses that can infect the cell.

In some preferred embodiments, the target is a viral component, preferably a component that is required for replication of the virus. Where the target is such a component, the aptamer that binds to that component preferably inhibits replication of the virus when the aptamer and the virus are present in the cell. In some preferred embodiments, the virus is a retrovirus, for example HIV-1. In those embodiments, one preferred target is the viral reverse transcriptase. Several aptamers targeting HIV-1 reverse transcriptase are known. See, e.g., Tuerk and Gold, 1992; Burke et al., 1996. In some preferred embodiments, the aptamer comprises a sequence selected from the group consisting of SEQ ID NO:1, SEQ ID NO:2, SEQ ID NO:3, SEQ ID NO:4, SEQ ID NO:5, and SEQ ID NO:6. In a more preferred embodiment, the aptamer comprises SEQ ID NO:2, 3 or 6, which are shown in the Examples as having strong antiviral activity.

As disclosed in Example 1, the aptamer having SEQ ID NO:2 can be encapsidated by HIV-1, which is believed to assist in its ability to inhibit replication of the virus. Accordingly, in some preferred embodiments, a target virus can encapsidate an aptamer targeted to a component of the virus.

The cells in which the RNA oligonucleotides of the present invention could be useful include eukaryotic as well as prokaryotic and archaeal cells. Preferably, the cell is a vertebrate cell. In more preferred embodiments, the cell is a mammalian cell; in the most preferred embodiments the cell is a human cell.

The aptamers useful as part of the RNA oligonucleotides can be selected by any means now known or later discovered. For example, the aptamer can be selected for a particular effect on a cell, or it can be selected for its ability to bind to a particular target. In preferred embodiments, the aptamer is selected by a SELEX process. As used herein, SELEX is a process for selecting aptamers that have high binding affinities for a particular target. In brief, the process generally involves (a) generation of a large library of aptamer oligonucleotides (e.g., having as much as $10^{15}$ different sequences); (b) exposing the library to the target of interest; (c) eliminating the library members that do not bind to the target; (d) amplifying the library members that bind to the target, creating a library enriched for aptamers that bind to the target; (e) repeating steps (b) through (d) as many as 15 times to isolate the aptamers that bind the most tightly to the target. As used herein, the SELEX process also includes various modifications now known (see, e.g., U.S. Pat. Nos. 5,472,841; 5,503,978; 5,567,588; 5,582,981; 5,637,459; 5,683,867; 5,705,337; 5,712,375; and 6,083,696) or later discovered.

The self-cleaving ribozymes can be of any form known in the art. Preferred sequences are provided herein as SEQ ID NOs:2, 3 and 6.

The RNA oligonucleotide of the present invention can also comprise a third ribozyme between the two self-cleaving ribozymes and adjacent to the aptamer, wherein the third ribozyme is not self-cleaving. In these embodiments, the third ribozyme can be either 5' to the aptamer or 3' to the aptamer on the RNA oligonucleotide. The third ribozyme can be directed to any target nucleic acid molecule that a ribozyme is now known or later discovered to cleave. In preferred embodiments, the third ribozyme is directed to the mRNA of a component of a cell or the RNA of a component of a virus. This third ribozyme can be directed to the same target as the aptamer, or a different target. Targeting the third ribozyme to the same target as the aptamer could be useful to provide additional inhibition of the target by inhibiting, for example, both the mRNA of the target (with the non-self-cleaving ribozyme) as well as any protein that is made from the mRNA (with the aptamer). Alternatively, the third ribozyme can be directed to a target different from the aptamer. A nonlimiting example of the use of a third ribozyme in the RNA oligonucleotides of the present invention is the use of an aptamer targeted to HIV-1 reverse transcriptase with a third ribozyme directed to the HIV-1 reverse transcriptase gene or the cellular gene encoding CD4. The targeting of both the aptamer and the third ribozyme to the same or different components of the same virus would be expected to avoid failure of control of the virus caused by the virus developing resistance to the function of either the aptamer or the third ribozyme.

Alternatively, the third ribozyme, or a second aptamer, can be present on the RNA oligonucleotide outside of the two self-cleaving ribozymes, preferably flanked by one of the two previously described self-cleaving ribozymes and a third self-cleaving ribozyme. Thus, nonlimiting examples of the configuration of the RNA oligonucleotide include 5'-S-A-S-A-S-3', 5'-S-A-S-R-S-3' and 5'-S-R-S-A-S-3', where S is a self-cleaving ribozyme, R is a non-self-cleaving ribozyme, and A is an aptamer. The use of a third, fourth, or more aptamers and/or non-self-cleaving ribozymes, optionally in conjunction with additional self-cleaving ribozymes, is also contemplated. Any of the aptamers and/or non-self-cleaving ribozymes can be identical to other aptamers and/or non-self-cleaving ribozymes present in the RNA oligonucleotide. As previously discussed, such configurations are useful for providing high levels of aptamers or non-self-cleaving ribozymes. The aptamers or non-self-cleaving ribozymes can also have different sequences, either binding to the same or to different targets. Those configurations usefully provide aptamers and/or non-self-cleaving ribozymes that complement each other, e.g., by both targeting a particular protein or two proteins in a biochemical pathway.

In related embodiments, the invention is directed to vectors encoding any of the above-described RNA oligonucleotides. In these embodiments, the vectors are useful for transfecting a cell, and thus can include a means for selecting or identifying cells that are transfected with the vectors, for example a G-418 resistance gene and/or a gene encoding β-galactosidase. The vector can also have appropriate polylinkers and/or other elements to facilitate engineering the vector, as well as promoters, enhancers, or other control elements, operably linked to the DNA encoding the RNA oligonucleotides, which control the timing and amount of expression of the RNA oligonucleotide. Included herein are any known or later discovered constitutive promoter or inducible promoter, allowing expression of the RNA oligonucleotide only under particular circumstances. Nonlimiting examples of a promoter include the CMV promoter (a viral promoter that uses pol II—see Examples 1 and 2), and, preferably, a tRNA promoter, for example tRNA$^{val}$ promoter (using pol III—see Example 2). Preferred vectors in these embodiments are viral vectors, however, any other vector, including plasmid vectors, that can facilitate transfection or selection for, or identification of, transfected cells expressing the RNA oligonucleotides is envisioned as within the scope of the invention. Nonlimiting examples of preferred vectors are adenoviral and retroviral vectors. Where the target is HIV-1, a particularly useful vector is a retroviral vector such as MuLV, for example a pBabe MuLV vector or an MMP-eGFP vector (see Examples 2 and 3). These MuLV vectors preferably have a long terminal repeat (LTR) driving expression of the vector. The aptamer in those vectors is preferably in opposite orientation from the LTR (see Example 3).

As used herein, "transfection" refers to the introduction of a nucleic acid molecule into a cell, including but not limited to a nucleic acid molecule within a viral or plasmid (i.e., naked DNA) vector. Thus, the term "transfection" encompasses the introduction of any vector into a cell, including viral or naked DNA vectors.

Additional embodiments include cells transfected with the above-described vectors. Preferably, the RNA oligonucleotides encoded by the vectors are expressed in these cells. Since aptamers and ribozymes would be expected to be functional in a cell of any organism, the cells in these embodiments can be from any prokaryotic or eukaryotic species, including without limitation bacteria, archaea, protists, fungi, plants, and animals, including vertebrates. Preferably, the cells are mammalian cells; most preferably the cells are human cells.

As used herein, "cells" is not limited to any particular cell type, and can include stem cells, such as hematopoietic stem cells, as well as any other type of cells that are amenable to transfection. The cell can be in culture, or alternatively, the cell can be part of a multicellular organism, preferably a mammal, such as a human. Where the cell is part of a multicellular organism, ex vivo treatment of the organism is envisioned, where the cell is transfected in vitro (e.g., in culture), then transplanted into the multicellular organism. Alternatively, the cell can be transfected with the vector in the multicellular organism (i.e., in vivo).

In some preferred embodiments, the aptamer expressed in the cell is capable of inhibiting replication of a virus in the cell. Some preferred viruses for these embodiments are retroviruses, such as HIV-1. Preferably, the virus is also able to encapsidate the aptamer. See, e.g., Example 1.

In similar embodiments, the invention is directed to cells expressing an aptamer, wherein the aptamer does not comprise flanking sequences that interfere with the aptamer function. The aptamer in these embodiments is preferably expressed within one of the RNA oligonucleotides previously described, i.e., comprising self-cleaving ribozymes that flank the aptamer sequence, where the self-cleaving ribozymes cleave the RNA oligonucleotide to release the aptamer.

As with the aptamers that are part of the RNA oligonucleotides previously described, the aptamers of these embodiments are not limited to those binding to any particular targets and can be targeted to, for example, a component of a cell or virus. Preferred examples have been previously enumerated.

The present invention is also directed to methods of inhibiting replication of a virus in a cell. The methods comprise transfecting the cell with a vector encoding one of the previously described RNA oligonucleotides, i.e., comprising an aptamer flanked by two self-cleaving ribozymes. In these embodiments, the aptamer is capable of binding to a component of the virus. As previously discussed, the aptamer can be targeted to any virus, for example a retrovirus such as HIV-1. When the virus is a retrovirus, a preferred target is a reverse transcriptase. Examples of such aptamers are provided in as described in Example 1 as SEQ ID NO:1, SEQ ID NO:2, SEQ ID NO:3, SEQ ID NO:4, SEQ ID NO:5, and SEQ ID NO:6.

More generally, the invention is directed to methods of treating an organism with an aptamer. The methods comprise transfecting a cell of the organism with a vector encoding one of the previously described RNA oligonucleotides, i.e., comprising an aptamer flanked by two self-cleaving ribozymes. The vectors, RNA oligonucleotides and aptamers have been previously described. Also as previously discussed, these methods are not limited to any particular organism and can be utilized with any prokaryote or eukaryote that is amenable to transfection. Additionally, where the organism is multicellular, ex vivo and in vivo embodiments are envisioned.

The present invention also provides for methods of determining whether a test aptamer is effective in inhibiting the function of a target of the aptamer in a cell. The methods first encompass transfecting the cell with one of the previously described vectors encoding an RNA oligonucleotide that comprises an aptamer flanked by two self-cleaving ribozymes. In these embodiments, the vector is capable of transfecting the cell and the aptamer encoded in the vector is the test aptamer. The cell or its components is then analyzed to determine whether the function of the target of the aptamer is inhibited in the cell.

These methods can be used with any cell capable of being transfected with the vectors, including any such prokaryotic or eukaryotic cell, e.g., mammalian cells such as human cells.

These methods are not narrowly limited to any particular type of analysis used to determine whether the function of the target of the aptamer is inhibited. The selection of the analysis depends on the type of target inhibited. Where the target is a small bioactive compound, such as an antibiotic or a toxin, the analysis preferably involves a determination of whether the effects of the compound is affected. For example, if the target is a toxin, the viability of the cell can be determined after toxin treatment of cells that have been transfected with the vector vs. cells that have not been transfected. Alternatively, the mechanism of the toxin's effect can be measured, e.g., membrane permeability or electron transport function. Where the target is a cellular protein, the analysis can involve a determination of the effect of the aptamer on the function of the protein, e.g., enzyme activity, ligand binding ability, etc.

When the target of the aptamer is a viral component, the effect of the aptamer is preferably determined by determining the effect of the aptamer on viral replication, for example by quantifying a viral component such as RNA or a viral protein, such as p24 in the case of HIV-1 (see Examples).

The present invention is also directed to RNA aptamers produced in a cell, wherein the aptamer is capable of binding to a target molecule, and wherein the aptamer is not covalently linked to a flanking sequence that interferes with the binding. These embodiments encompass the previously described aptamers that are part of the RNA oligonucleotides comprising the aptamer flanked by two self-cleaving ribozymes. In preferred embodiments, the RNA oligonucleotide is transcribed from a vector that was transfected into the cell, and the aptamer is cleaved from the RNA oligonucleotide by the self-cleaving ribozymes. As previously discussed, the aptamer can also be covalently linked to a non-self-cleaving ribozyme. Alternatively, the non-self-cleaving ribozyme, or additional aptamers, that are not covalently linked to the aptamer can be present in the cell. Potential targets and cell types of these aptamers have been previously discussed.

Related embodiments of the present invention include methods of expressing an RNA aptamer in a cell. The methods comprise transfecting the cell with any of the previously described vectors that encode a vector encoding an RNA oligonucleotide that comprises an aptamer flanked by two self-cleaving ribozymes. Cell types and species, methods of transfection, and aptamer targets have all been previously discussed.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples.

In accordance with the present invention, there may be employed conventional methods of molecular biology, microbiology, and recombinant DNA techniques within the skill of the art. Such techniques are explained fully in the literature. See, e.g., Maniatis, Fritsch & Sambrook, "Molecular Cloning: A Laboratory Manual" (1989); "Current Protocols in Molecular Biology" Volumes I-IV (Ausubel, R. M., ed. (1997); Myers, "Molecular Biology and Biotechnology: A Comprehensive Desk Reference" (1995) and "Cell Biology: A Laboratory Handbook" Volumes I-III (J. E. Celis, ed. (1994).

Example 1

Inhibition of HIV-1 Replication by Aptamers Expressed in HIV-1 Infected Cells

Introduction

Inhibitors that target HIV-1 reverse transcriptase (RT) used in current highly active anti-retroviral therapy (HAART) regimens can block viral replication and retard the onset of AIDS. However, toxicity (Brinkmann et al., 1999) and the rapid appearance of drug resistant viral strains (Richman, 2001) are serious concerns and diminish their merit. Current anti-RT drugs have exploited the presence of two binding pockets on this viral DNA polymerase. The nucleoside analog RT inhibitors (NRTI) bind to the deoxynucleoside triphosphate (dNTP)-binding pocket, which is formed partly by the template-primer nucleic acid and partly by the protein surfaces (Tantillo et al., 1994). The other site, the non-nucleoside RT inhibitor (NNRTI)-binding pocket, is a hydrophobic pocket exclusively present in the RT of the M subgroup of HIV-1 (Id.). A key surface on the RT, the template.primer-binding cleft, in spite of its central importance in viral reverse transcription has been minimally explored as a target to obstruct viral replication.

Small nucleic acid aptamers with high affinity to HIV-1 RT were previously isolated in vitro from a library of randomized DNA/RNA sequences via the SELEX procedure (Systematic Evolution of Ligands by EXponential enrichment) (Burke et al., 1996; Ellington and Szostak, 1990; Scfhneider et al., 1995; Tuerk and Gold, 1990; Tuerk and Gold 1992). The anti-RT aptamers are small RNA molecules that lack primary sequence homology to each other, display high affinity and specificity to HIV-1 RT, and competitively inhibit its enzymatic activity in vitro. Thus, their three dimensional structures all recognize the same surface on the RT, the template primer-binding cleft. Some of the anti-HIV-1 RT aptamers have the potential to form pseudoknot-like secondary structures often with a sharp bend reminiscent of the conformation of template.primer bound to HIV-1 RT (Burke et al., 1996). The crystal structure of HIV-1 RT bound to one of the RNA aptamers shows that the aptamer makes extensive contacts with the template-primer cleft of RT (Jaeger et al., 1998). It has been shown that the association constant of such aptamers to HIV-1 RT correlates with the degree of inhibition. Thus, these aptamers are termed here "template analog RT inhibitors" (TRTIs).

Despite the unique nature of the anti-HIV-1 RT RNA aptamers, their utility as inhibitors of viral replication has remained unexploited until now. Therefore, we examined their suitability for intracellular expression via gene delivery and their ability to block HIV replication. In this report, we show that such aptamers efficaciously block HIV-1 replication in cell culture. The aptamers block an early stage of viral life cycle; inhibit drug-resistant viruses as well a several subtypes of HIV-1. Furthermore, we report that even under potent onslaught, such as a high ratio of virions to cells, HIV could be effectively blocked by the intracellularly expressed TRTI aptamers.

Materials and Methods

Anti-RT Aptamers. The anti-HIV-1 RT aptamers used for this study were selected from Tuerk et al. (1992) and Burke et al. (1996) and include RNA aptamers 1.1 (SEQ ID NO:1); 70.8,13 (SEQ ID NO:2); 70.12,16; 70.15 (SEQ ID NO:3); 70.24,67; 70.28 (SEQ ID NO:4); 70.28t34 (SEQ ID NO:5); 80.10; 80.18; and 80.55,65 (SEQ ID NO:6). The construction of the aptamer cassette (FIG. 1) with the flanking ribozymes was essentially as described previously by Benedict et al. (1998) except that EcoRI and ApaI restriction sites were present between the two ribozymes placed under the control of CMV promoter within the vector pcDNA3.1 (Invitrogen, Carlsbad, Calif.). Double stranded adapters encoding different aptamer sequences were inserted via ligation between the EcoRI and ApaI sites.

In vitro binding. RNA aptamers for RT-binding studies were generated by in vitro transcription using T3 RNA polymerase. The T3 promoter was linked to each of the ribozyme-aptamer-ribozyme sequences via PCR using the upstream primer T3-Start, 5'AATTAACCCTCACTAAAGGGTAGA-CAATTCACTGC3' (SEQ ID NO:9) and the downstream primer pcDNA3.1END, 5'GCATGCCTGCTATTGTCT-TCCC3' (SEQ ID NO:10). PCR products thus generated using each ribozyme-aptamer-ribozyme construct and served as the template for in vitro transcription using the Ambion (Austin, Tex.) MEGAshortscript kit. The transcripts were radiolabeled internally with $[\gamma\text{-}^{32}P]$-UTP, the reaction products resolved on a 10% denaturing polyacrylamide gel.

Radiolabeled, processed RNA aptamers were gel purified and eluted in 500 mM $NH_4OAc$/1 mM EDTA/0.2% SDS. RNA was then treated with phenol/chloroform and ethanol precipitated. Electrophoretic mobility shift assays were performed by incubating 10 fmol purified RNA aptamer with increasing amounts of purified HIV-1 RT at 25° C. in 10 µl of buffer containing 50 mM KCl, 25 mM NaCl, 5% glycerol, 300 µg/ml BSA. The reaction products were electrophoresed on native polyacrylamide gels. Dried gels were exposed to a phosphorimager screen and Kd calculated by using the ImageQuant software. To determine the binding strengths, the percentage of band shift observed with increasing concentrations of RT (1 nM to 500 nM), with respect to the no protein control lane, was first determined. The $K_d$ values were determined by fitting data from three independent experiments to a dose response curve using nonlinear regression (Cann 1996) (GraphPad Software Inc.).

In vitro RT inhibition. To determine the $IC_{50}$ values, self-cleaved RNA aptamers were gel purified and eluted in 500 mM $NH_4OAc$/1 mM EDTA/0.2% SDS. RNA was then treated with phenol/chloroform and ethanol precipitated. RT reactions (50 µl) contained 80 mM KCl, 50 mM Tris-Cl (pH 8.0), 6 mM $MgCl_2$, 1 mM dithiothreitol (DTT), 0.1 mg/ml BSA, 10 µM $[\gamma\text{-}^{32}P]$ dTTP, 25 µM each of the remaining three dNTPs, and a range of concentrations of RNA aptamers (1 nM to 1000 nM). Reactions were incubated at 37° C. for 15 min. Reactions initiated by the addition of 25 ng of purified HIV-1 RT and at the end of the reaction, aliquots were spotted onto DE81 filter paper and washed with 2×SSC (30 mM Sodium Citrate, 300 mM NaCl pH 7.0). Dried filters were then counted and individual $IC_{50}$s were determined by fitting results to a dose-response curve using nonlinear regression (GraphPad Software Inc., San Diego, Calif.).

Cells and viruses. Drug resistant HIV isolates and different subtypes of HIV-1 were obtained from the NIH AIDS Research and Reference Reagent program. The different viruses resistant to the respective drugs are listed below with the NIH reagent program catalog numbers and contained the mutations indicated: AZT$^r$ (#2529) with L74V/M41L/V106A/T215Y, 3TC$^r$ (#2970) with M184V, ddI$^r$/ddC$^r$ (#2528) with L74V, Nevirapine$^r$/TIBO$^r$ (#1413) with K103N and Y181C mutations and the protease inhibitor-resistant virus (resistant to multiple anti-HIV protease drugs; #2840) carrying the mutations L10R/M46I/L63P/V82T/I84V and resistant to multiple PIs) class of drugs.

Viral titers were determined by p24 assay and m.o.i. calculated using P4 cells. Aptamer-expressing Jurkat cells were infected at an m.o.i. of 0.1 and viral kinetics monitored by p24 antigen measurements over a period of 18-20 days. The p24 measurements were via the antigen capture assay using a commercial p24 ELISA (NEN) according to manufacturers instructions.

To generate clonal cell lines stably expressing each of the aptamer RNAs, purified plasmid DNA was transfected into 293T and Jurkat cells using the GenePorter reagent (Gene Therapy Systems, San Diego). Stable ribozyme/aptamer cell lines were selected using 500 μg/ml G418 (Invitrogen, Carlsbad, Calif.). For 293T cells, multiple G418-resistant colonies were separately expanded and expression of the respective aptamer RNA confirmed by RPA. For Jurkat T cells, 12 hours after the start of drug selection, cells were cloned by dilution, single cell clones expanded and the expression of aptamer RNA confirmed.

Ribonuclease Protection assay. We examined the cytoplasmic RNA of 293T cells expressing various aptamers by ribonuclease protection assay (RPA). RPA analysis was performed using the RPA III kit (Ambion, Tex.) according to the manufacturer's instructions. Briefly, cytoplasmic RNA was extracted from aptamer-expressing 293T cell lines by Trizol (Invitrogen, Carlsbad Calif.). In vitro transcripts corresponding to the aptamer sequences were generated by T3 RNA polymerase. The aptamer sequences were flanked by sequences unrelated to those present in the ribozyme constructs. Each protection assay was performed on equal amounts of cytoplasmic RNA (10 μg) using $4 \times 10^4$ cpm of the corresponding antisense aptamer probe internally labeled with [γ-$^{32}$P]-UTP. Reactions were heated to 95° C. for 5 min and then incubated overnight at 42° C. The digestion of the single stranded sequences was carried out using a mixture of RNase T1 and RNase A for 30 min at 37° C. Protected fragments were analyzed by electrophoresis through an 8% denaturing polyacrylamide gel and were quantified directly using a phosphoimager. Each sample was also probed with an antisense probe to human β-actin (Ambion, Tex.).

Western Blot analysis. Virion particles released from aptamer-expressing 293T cells were collected from filtered supernatants and were concentrated by centrifugation through a 25% sucrose cushion in TNE at 4° C. for 2 h at 23,000 rpm. Pelleted virus was resuspended in PBS for RNA extraction for dot blot analysis or in 50 mM Tris-HCl (pH 7.4), 100 mM dithiothreitol, 50 mM KCl, 0.025% Triton-X 100 and 2% sodium dodecyl sulfate for western blot analysis. The latter was boiled for 5 min and run on a 12% SDS-polyacrylamide gel. Viral proteins were transferred to nitrocellulose and the western blot was probed with anti-HIV-1 IgG (NIH AIDS Research and Reference Reagent program).

Dot blot analysis. RNA was extracted from purified virus particles by Trizol (Invitrogen). Total RNA was blotted on to Hybond Nylon membrane (Amersham) and probed for viral genomic RNA, aptamer RNA and tRNA$^{lys,3}$ with antisense oligonucleotides probes. The aptamer probe consisted of a pool of six different oligonucleotides. The oligonucleotides were end-labeled with [γ-$^{32}$P]-ATP using polynucleotide kinase and hybridized to the target RNA in Ultrahyb buffer as suggested by the manufacturer (Ambion).

Measuring infectivity and replication capacity of HIV. Reporter cell lines with lentiviral tat-driven expression of luciferase (CEM-LuSIV cells (Roos et al., 2000)) or β-galactosidase (P4-HeLa cells (Charneau et al., 1994)) were used to quantitate viral infectivity. Equal inputs of virus (10 ng of p24) were used to infect CEM-LuSIV cells and 24 hours later, the cell lysate was assayed for luciferase activity (Promega, Madison, Wis.) using a Luminometer. The output obtained was in relative light units (RLU). Virus equivalent to 25 ng of p24 was used to infect P4-HeLa cells and 36 hours post-infection, the cells were fixed in 0.1% glutaraldehyde and stained with X-gal. P4-HeLa cells were used to calculate the multiplicity of infection (m.o.i.).

Wild type HIV-1 was generated by transfecting a replication competent and infectious molecular clone of HIV-1$_{R3B}$ into 293T cells. The supernatant was assayed for virus and multiplicity of infection tested on P4-HeLa cells. Aptamer expressing Jurkat cell lines were infected at an m.o.i of 0.1 and viral kinetics monitored as by p24 antigen production.

Results

Design of aptamer expression system. Although both DNA and RNA aptamers have been described (Burke et al., 1996; Schneider et al., 1995; Tuerk and Gold, 1992), the RNA aptamers are advantageous since they can be introduced into cells via gene therapy-based approaches. A large number of RNA aptamers have been isolated but their utility for blocking HIV replication is untested. We surmised that RNA aptamers with the strongest affinity to RT in vitro would also efficiently inhibit HIV replication. On the basis of their relative binding capacity to RT, we selected 10 aptamer sequences from those described by Tuerk and Gold (1992) and Burke et al. (1996).

Figure 2:
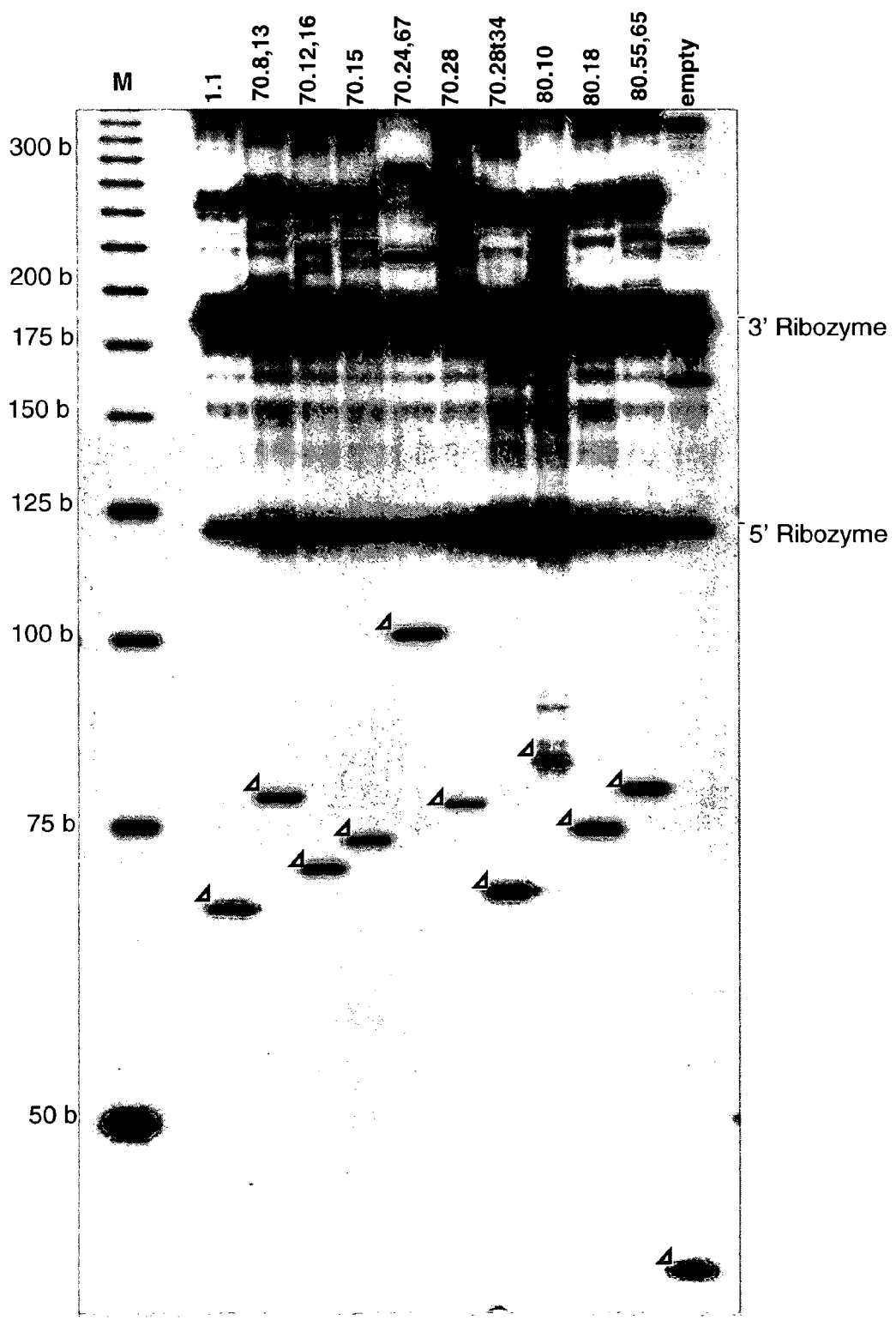
FIG. 2 is an autoradiograph of a denaturing PAGE gel showing the radiolabeled products of T3 RNA polymerase-mediated in vitro transcription of a ribozyme-aptamer-ribozyme construct of the present invention. The 5'- and 3'-flanking ribozyme fragments (118 nt and 193 nt respectively) released by self-cleavage are indicated accordingly. The sizes of the liberated aptamer fragments ranges from 66 nt to 101 nt and they are indicated by arrowheads. The empty vector releases a 44 nt fragment containing just the flanking ribozymes and the linker sequence containing the restriction sites (rightmost lane).

As the selectivity of RNA aptamers is directly related to its three-dimensional structure, unrelated flanking sequences are likely to interfere with the proper folding and need to be minimized. Therefore, we created an expression vector in which the aptamer sequence was flanked by self-cleaving ribozymes (FIG. 1). The ribozymes were designed to recognize the GUC cleavage motifs that were present in the primary transcript immediately bordering the aptamer sequence. Upon cleavage by the ribozymes, the aptamer RNA is released. The in vitro transcripts of the selected aptamers were analyzed on a polyacrylamide gel. Efficient processing of the ribozymes (>50% fully processed for all aptamers) was observed in each case, releasing the aptamer RNA and the 5' and the 3' ribozyme fragments (FIG. 2).

Figure 3:
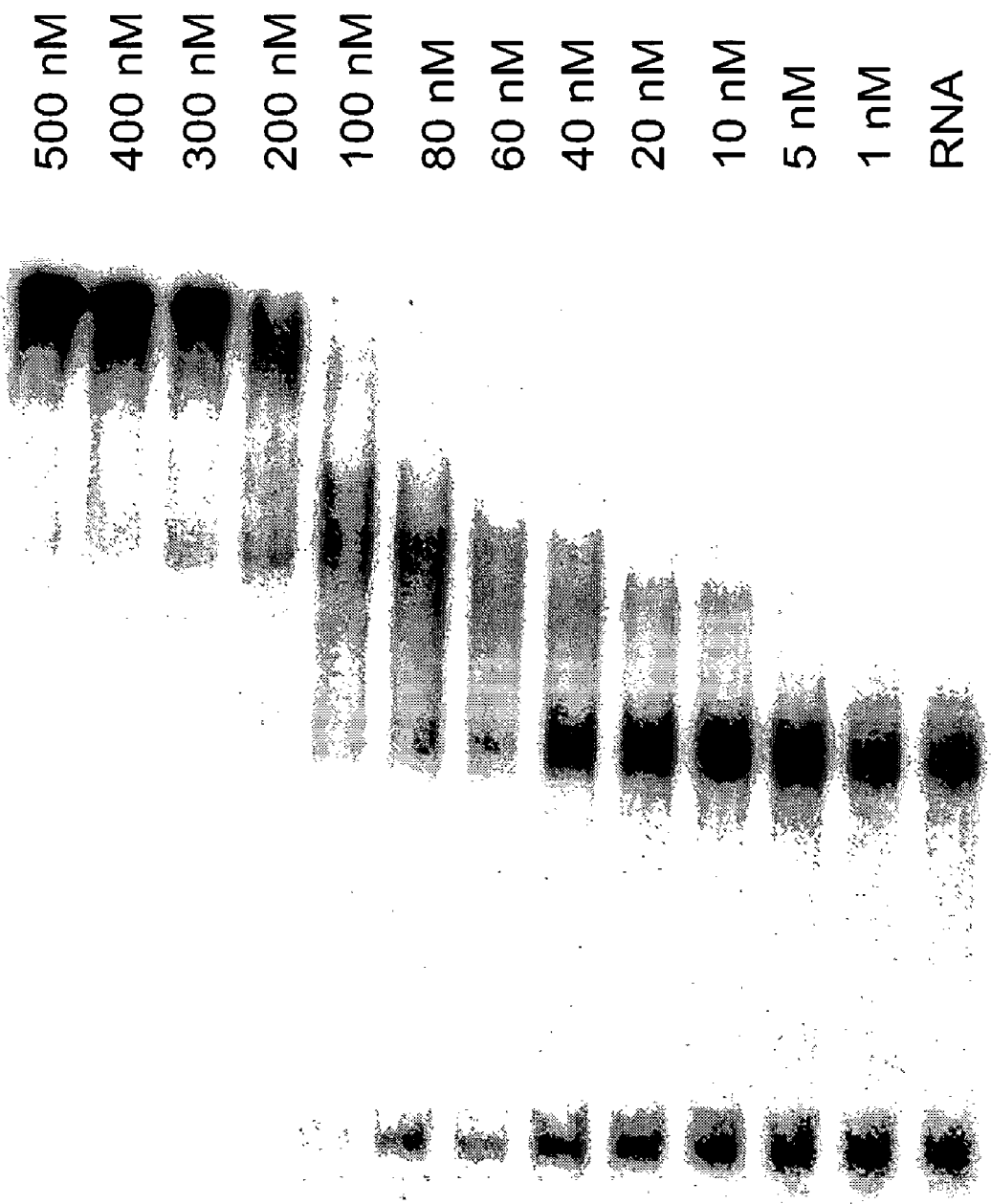
FIG. 3 is an autoradiograph of a native PAGE gel showing electrophoretic mobility shift of the radiolabeled RNA aptamer 80.55,65 (SEQ ID NO:6) upon binding to increasing concentrations of purified, recombinant HIV-1 RT (1 nM to 500 nM). The bands that represent free RNA can be seen in the lane marked 'RNA' which represents the aptamer incubated in the absence of RT. All bands above the major band in the 'RNA' lane represent those complexed with HIV-1 RT.

Identifying the most potent of RT aptamers. We hypothesized that the strongest-binding aptamer would also be the most potent inhibitor of HIV replication. Therefore, the ability of each of the 10 selected RNA aptamers to bind recombinant purified HIV-1 RT was evaluated in vitro via an electrophoretic mobility shift assay (EMSA) and the dissociation constants determined for each individual aptamer in its processed form. In vitro transcription of the primary transcripts, with T3 RNA polymerase was followed by gel purification of the processed aptamers. The aptamer RNAs were incubated with increasing concentrations of purified recombinant HIV-1 RT, the reactions were resolved on a non-denaturing polyacrylamide gel (FIG. 3) and K$_d$ values calculated based on the degree of band shift caused by the formation of RNA-protein complexes (see Methods section). The binding affinities calculated ranged from 27 nM to 2001 nM (Table 1).

TABLE 1

Dissociation constants ($K_d$) of various aptamers for interaction with HIV-1 RT and their ability to inhibit RT activity in vitro ($IC_{50}$).

| RNA Aptamer-SEQ ID NO: | $K_d$, nM | $IC_{50}$, nM | Length, nt* |
| --- | --- | --- | --- |
| 70.8,13-SEQ ID NO: 2 | 27 | 89 | 78 |
| 70.15-SEQ ID NO: 3 | 63 | 159 | 73 |
| 80.55,65-SEQ ID NO: 6 | 129 | 143 | 79 |
| 70.12,16 | 184 | 210 | 71 |
| 70.28-SEQ ID NO: 4 | 201 | 254 | 77 |
| 80.10 | 180 | 309 | 89 |
| 70.28t34-SEQ ID NO: 5 | 219 | 327 | 67 |
| 80.18 | 197 | 334 | 74 |
| 1.1-SEQ ID NO: 1 | 270 | 607 | 65 |
| 70.24,67 | 2001 | >1000 | 101 |

*The length of the nucleotides includes short, 5'- and 3'-flanking sequences of 12 and 11 nucleotides, respectively.

Next, the ability of each of the 10 selected RNA aptamers to inhibit recombinant purified HIV-1 RT was evaluated in vitro and the degree of inhibition ($IC_{50}$) by each aptamer was determined. In vitro transcription of the primary transcripts with T3 RNA polymerase was followed by gel purification of the processed aptamers. The $IC_{50}$s calculated ranged from 89 nM to >1000 nM (Table 1). Six RNA aptamers were selected for further studies, to test their effectiveness in inhibiting HIV-1 replication. Of these, 70.8,13 (SEQ ID NO:2), 70.15 (SEQ ID NO:3) and 80.55,65 (SEQ ID NO:6) were the three best binders (with $K_d$ values of 27 nM, 63 nM and 129 nM respectively) (Table 1). Furthermore, these three aptamers were also the best inhibitors of HIV-1 RT in our in vitro assays, displaying $IC_{50}$ values of 89, 143 and 159 nM respectively (Table 1). The other three aptamers 70.28 (SEQ ID NO:4) (254 nM), 70.28t34 (SEQ ID NO:5) (327 nM) and 1.1 (SEQ ID NO:1) (607 nM) were selected because they were previously shown by other laboratories to have a high specificity and tight binding to HIV-1 RT (Burke et al., 1996; Kensch et al., 2000).

Figure 4:
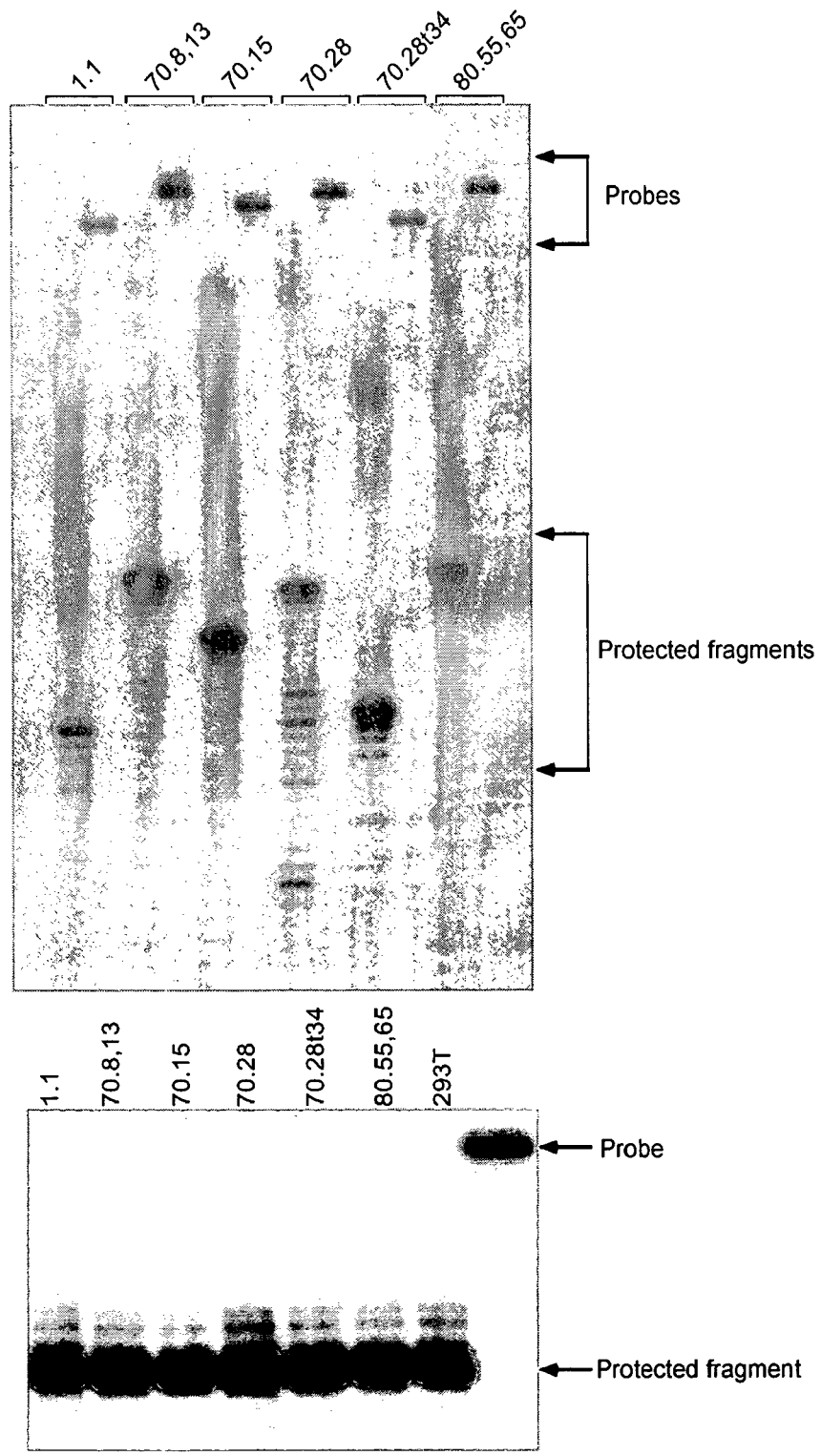
FIG. 4 is an autoradiograph of a denaturing PAGE gel showing the protected radiolabeled RNA fragments corresponding to each of the six aptamer RNAs in the cytoplasm of the respective cell lines. Probes and protected fragments are indicated. As an internal control, cytoplasmic RNAs were also probed for the levels of human β-actin mRNA.

Intracellular levels of aptamers. In order to ensure that the aptamer transcripts are expressed at significant levels within the 293T transfectants, we isolated cytoplasmic RNA from each of the 6 cell lines and performed RNase protection assays. Intensity of the protected fragment corresponds to the cytoplasmic level of the respective aptamer RNA (a sum of the processed and unprocessed forms). As a control for loading, we also probed the same RNA preparations for the level of transcripts of the housekeeping gene β-actin. These results are shown in FIG. 4. When the protected fragments for each aptamer were quantitated as a percentage of the level of actin transcripts for the respective cell line, the aptamers were found to be at 7%, 34%, 22%, 7.7%, 34% and 5.6% for the aptamers 1.1 (SEQ ID NO:1), 70.8,13 (SEQ ID NO:2), 70.15 (SEQ ID NO:3), 70.28 (SEQ ID NO:4), 70.28t34 (SEQ ID NO:5) and 80.55,65 (SEQ ID NO:6), respectively. Thus, variation in the level of expression of these aptamers is within 6-fold of each other.

Figure 5A:
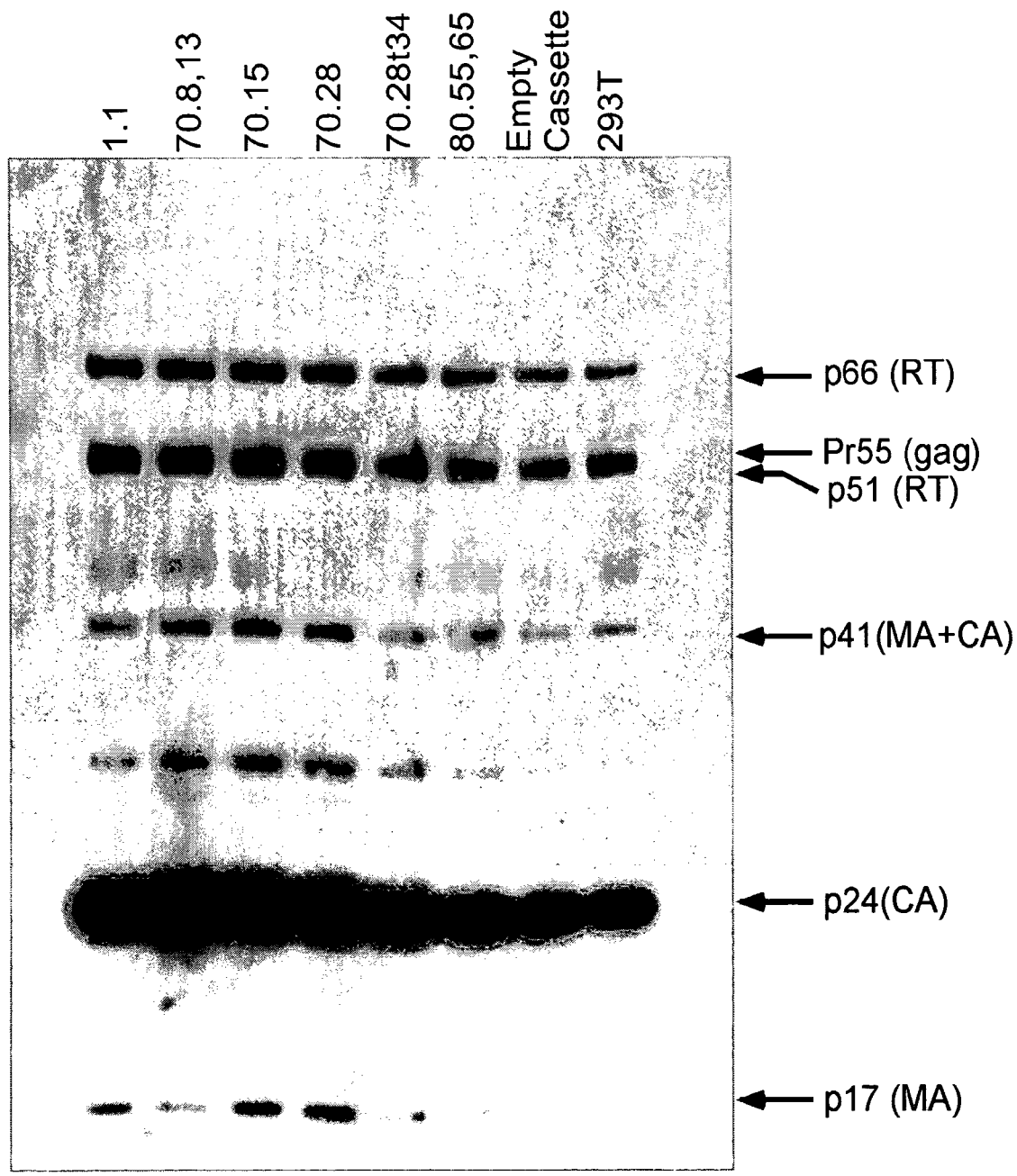
FIG. 5 are two autoradiographs showing the results of an analysis of virion proteins and of RNAs encapsidated by virions. Panel A is an autoradiograph showing the results of a study where virion proteins were extracted from studied viruses, resolved on an SDS-PAGE gel containing a 4% to 20% gradient of polyacrylamide, then immunoblotted with anti-HIV antisera (Human HIV immunoglobulin). Panel B is an autoradiograph of dot blot hybridizations of virus particles harvested from aptamer-expressing 293T cells. Total RNA from purified virions spotted on nitrocellulose is hybridized to oligonucleotide probes specific for viral genomic RNA, aptamer RNA and tRNA$^{Lys}_3$. The 'Empty' and '293T' correspond to virus released from cells expressing the empty, dual ribozyme transcript and that produced in plain 293T cells.

Effect of aptamers on the assembly and production of HIV. In order to assess the effect of these aptamers on viral replication, 293T cell lines stably expressing each ribozyme-aptamer were transfected with an infectious molecular clone of HIV-$1_{R3B}$ and the virus harvested 36 h post transfection. Quantitation of the virus released via measurement of p24 released revealed that there were no significant differences in the amount of virus produced between parental 293T cells and the ones expressing aptamers. Immunoblot analysis of viral proteins in the medium indicated that there was no noticeable difference between the viral proteins from the aptamer expressing cell lines and the controls (FIG. 5A), indicating that the assembly or maturation of the virus particles was not affected. These results reveal that the presence of the aptamer in the producer cells does not interfere with virus production or maturation.

Since the TRTI aptamers were identified as molecules capable of tightly binding to mature HIV-1 RT, we surmised that they could be packaged in the virions. However, the ability of aptamers to bind to RT in its unprocessed precursor form, the Gag-Pol polyprotein, has not been demonstrated earlier. Therefore, we tested if the aptamers are packaged into the virions via their ability to bind to Gag-Pol polyprotein. Purified virions were obtained from culture supernatants of aptamer-expressing cell lines by density-gradient centrifugation. Viral pellets were lysed and total RNA extracted. Dot blots of the total RNA were probed with anti-sense labeled oligonucleotides to confirm the presence of the aptamers. In every case tested, the aptamer was detected in the mature viral particles indicating that aptamers are indeed able to bind to Gag-Pol (FIG. 5B).

It is known that the HIV virions specifically encapsidate $tRNA^{lys3}$ and one of the determinants of this specificity is the RT within the Gag-Pol polyprotein (Mak et al., 1997). Therefore, we wondered if the binding of aptamers to RT portion of Gag-Pol precludes the encapsidation of $tRNA^{lys3}$. Our dot blot hybridizations reveal that along with the viral RNA, the cognate $tRNA^{lys3}$ primer was also present in the virions suggesting that packaging of aptamers does not preclude the packaging of tRNA (FIG. 5B).

Figure 6:
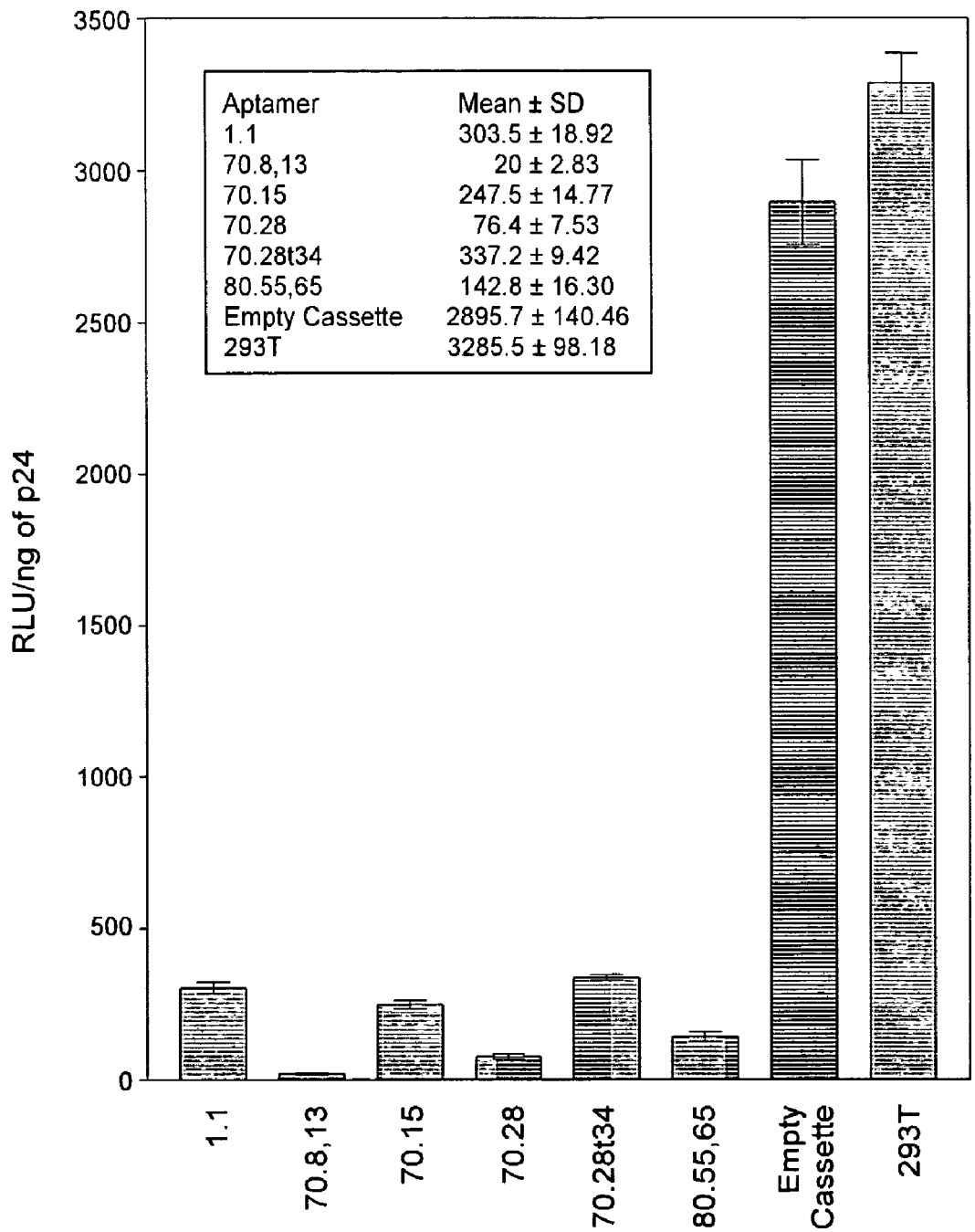
FIG. 6 is a bar graph showing the infectivity of virus harvested following transfection with a molecular clone of HIV into 293T cell lines stably expressing each of six aptamers. The infectivity of the virus was determined by infection of LuSIV cells as described in Example 1 under Materials and Methods. The bars represent the mean of three independent determinations and the standard deviations (shown in tabular format in the inset).

Aptamers inhibit HIV infectivity via an early block to reverse transcription. The infectivity of the virus particles released from aptamer-expressing cells was assayed using the CEM-LuSIV indicator cell line (Roos et al., 2000) which contains the luciferase reporter gene that is responsive to Tat protein. Virus particles obtained from all cells expressing the aptamers displayed a dramatic reduction in infectivity that ranged from 90% to 99% as compared with the control virus harvested from the parental 293T cells (FIG. 6). Of all the aptamers tested, the aptamer 70.8,13 (SEQ ID NO:2) which was the strongest RT inhibitor in vitro ($IC_{50}$: 89 nM), displayed the most dramatic reduction in infectivity (99%) (FIG. 6). Results obtained with an alternate indicator cell line, the HeLa-P4 cells, were comparable to that from LuSIV cells (data not shown).

In order to delineate the stage of the virus life cycle at which the aptamers were exerting their inhibitory influence in Jurkat cells, we selected three aptamers, 70.8,13 (SEQ ID NO:2), 70.15 (SEQ ID NO:3) and 80.55,65 (SEQ ID NO:6) which showed the strongest levels of inhibition in vitro ($IC_{50}$s: 89, 143 and 159 nM respectively). The virion particles were harvested from 293T cell lines expressing each of these aptamers. Jurkat T cells were infected with virions, total genomic DNA was extracted 12 h post-infection and subjected to reverse transcription stage-specific PCR to determine the extent of reverse transcription at three key steps in viral reverse transcription (Zack et al., 1990) (FIG. 7). Our results indicate that the synthesis of the earliest intermediate, the minus strong-stop DNA synthesis, was unaffected by the presence of any of the six aptamers in the virus (FIG. 7A). However, continued viral DNA synthesis as assessed by minus strand transfer product (FIG. 7B) and the formation of completed proviral DNA (FIG. 7C) were not evident for virions produced in the presence of the aptamers 70.8,13 (SEQ ID NO:2) and 70.15 (SEQ ID NO:3), suggesting that in these two cases the aptamer blocks reverse transcription in its early stages. Even though the other promising aptamer 80.55, 65 (SEQ ID NO:6) appeared to not completely prevent synthesis of proviral DNA, our data reproducibly show a considerable reduction in the level of DNA synthesized (FIG. 7C, lane 3).

Figure 8A:
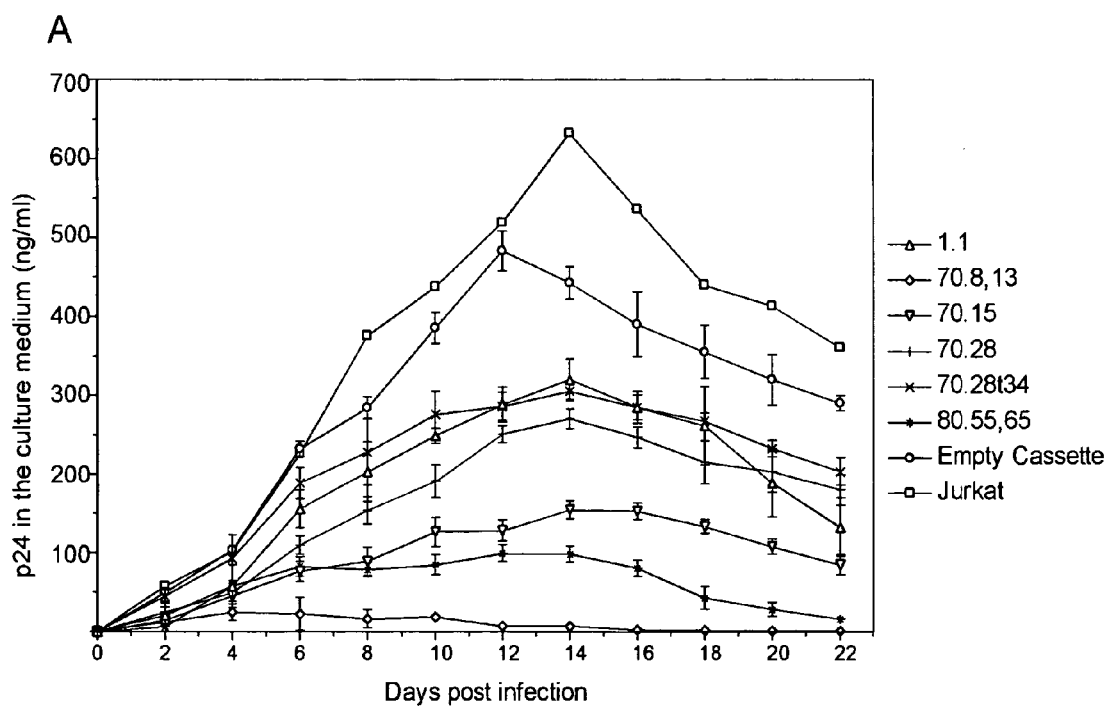
FIG. 8 shows graphs summarizing results of experiments to determine the replication kinetics of HIV-1 in Jurkat cells expressing RNA aptamers. Panel A shows the patterns of inhibition of HIV-1 replication in Jurkat cells expressing various RNA aptamers. Subsequent to infection at an m.o.i. of 0.1, Jurkat cell lines expressing each of the six aptamers, the parental Jurkat cell line and the control cell line (Empty Cassette) were maintained for 22 days. The data for Jurkat cell lines expressing each of the aptamers and the control cell line represents an average of measurements made on three independently derived cell lines. HIV in the culture medium was monitored via p24 determination every two days. Panel B shows infection of Jurkat T cell lines expressing the three best aptamers at a high multiplicity of infection. The Jurkat cell lines expressing the empty cassette and the aptamers 70.8,13 (SEQ ID NO:2), 70.15 (SEQ ID NO:3) and 80.55,65 (SEQ ID NO:6) were infected with 50 m.o.i. of HIV. The ratio of the infectivity of the virus in the medium (as measured by RLU on LuSIV indicator cells) per nanogram p24 is presented for 4, 8, 12 and 16 days.

Anti-RT aptamers limit the spread of virus in cultured T cells. In order to estimate the potential of the aptamers to suppress successive virus replication cycles, stable Jurkat cell lines expressing each of the six aptamers were generated. These stable cell lines were infected with wild type HIV-$1_{R3B}$ at a low m.o.i (0.1). Spread of the virus in the culture was then monitored by measuring p24 in the culture supernatants. In each case, the aptamers exerted a significant influence on the dynamics of viral replication and the propagation of infectious virus was severely compromised in stable cell lines expressing the aptamers 70.8,13 (SEQ ID NO:2), 70.15 (SEQ ID NO:3) and 80.55,65 (SEQ ID NO:6) (FIG. 8A). While the peak p24 production in the absence of the aptamers was observed at day 14, there was a range of levels of inhibition in the presence of various aptamers. The most dramatic inhibitory effect was observed in the case of aptamer 70.8,13 (SEQ ID NO:2) where the virus production was very minimal from the onset of infection (FIG. 8A). In fact, for this aptamer (70.8,13), virtually no detectable p24 was present in the culture supernatant up to 22 days. In order to ensure that the differences between different virus growth curves (in the absence of aptamer and the presence of different aptamers) are significant, we have performed Student's t-test for p24 values for day 14 (which represents the peak virus production for plain Jurkat cells). In repeated measures test, for all the cultures in parallel, this yielded a p value of <0.0001. When paired tests were performed between the 'Empty cassette' and viruses growing in the presence of each aptamer, for the same time point, all p values obtained were <0.0017, showing that the differences are significant.

Figure 8B:
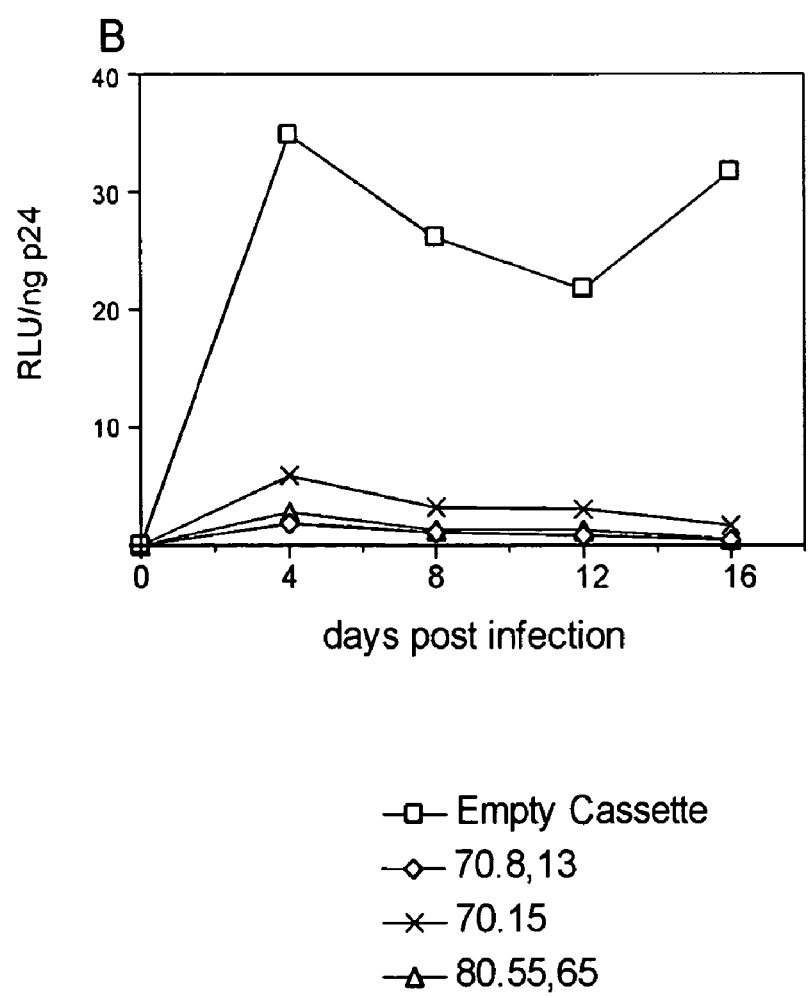

For such dramatic results to be effective in HIV-infected individuals, the aptamers should be able to thwart infection by much higher levels of virus input than tested here. Therefore, Jurkat cells expressing aptamers 70.8,13 (SEQ ID NO:2), 70.15 (SEQ ID NO:3) and 80.55,65 (SEQ ID NO:6) were challenged with HIV-$1_{R3B}$ at an m.o.i. of 50. Cells were cultured for 16 days and the virus output and its infectivity were measured via p24 antigen capture and LuSIV reporter assays respectively at regular intervals of 4 days. When the ratio of infectivity per particle (relative light units per ng p24) was measured for virus released from each of the aptamer-expressing Jurkat cells, it appeared that the infectivity of the viruses in the supernatant was severely reduced in comparison with parental Jurkat cells (FIG. 8B).

Figure 9A:
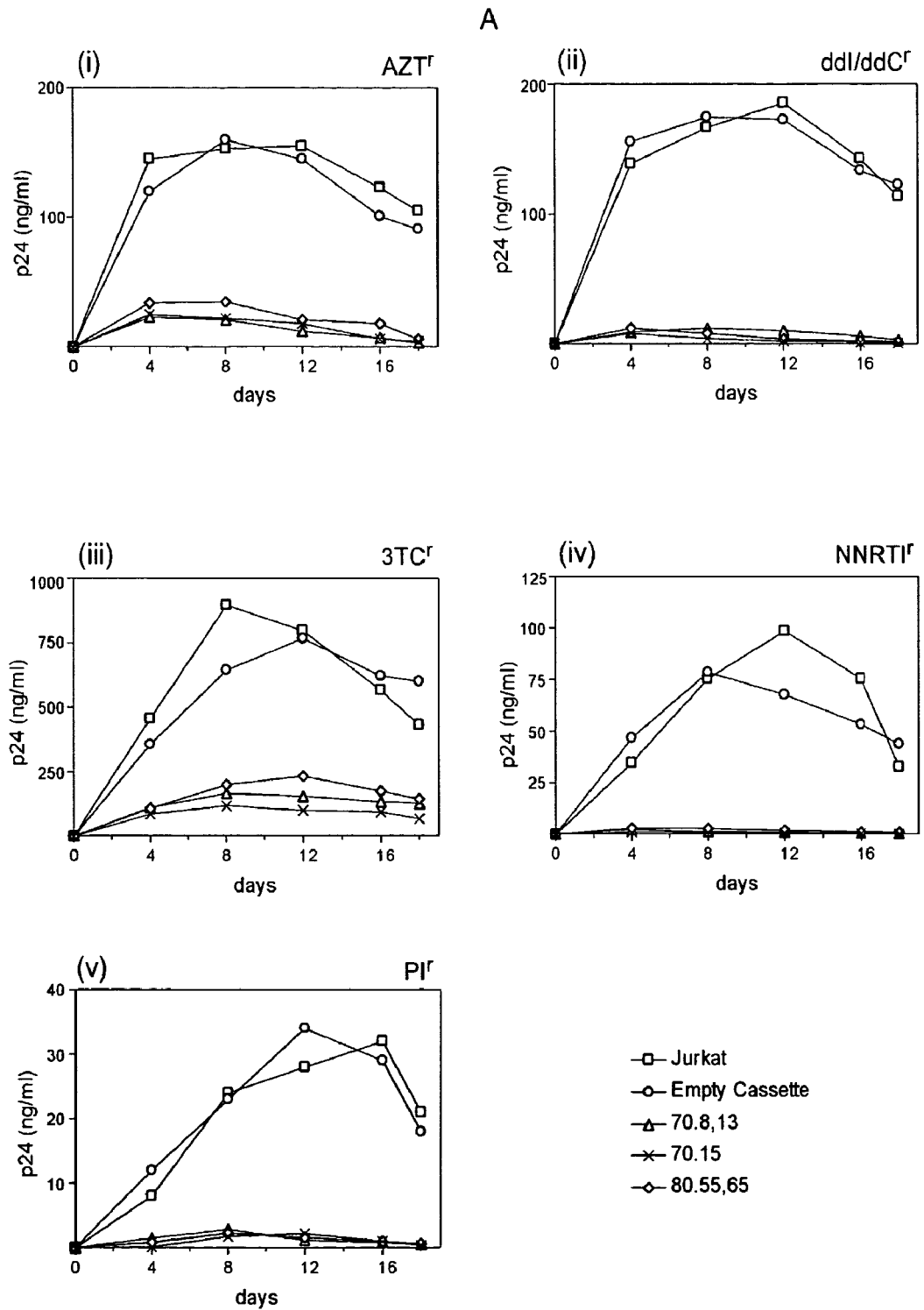
FIG. 9 shows graphs that summarize results of experiments to determine the ability of TRTI aptamers to inhibit drug-resistant variants and multiple subtypes of HIV. Panels A (i)-(v) shows the inhibition of drug-resistant isolates of HIV. Jurkat cell lines expressing the RNA aptamers 70.8,13 (SEQ ID NO:2), 70.15 (SEQ ID NO:3) and 80.55,65 (SEQ ID NO:6) were infected with (i) AZT-resistant, (ii) 3TC resistant, (iii) ddI/ddC resistant, (iv) NNRT resistant, and (v) protease resistant viral strains of HIV-1 at an m.o.i. of 0.1. Panel B shows the inhibition of different HIV subtypes by RNA aptamers. The same three cell lines were infected with HIV isolates of subtypes A (i), D (ii), E (iii), F (iv), C (v), 0 (vi) and A/D (vii) viral strains of HIV-1 at an m.o.i. of 0.1. Viral spread in both cases was monitored by p24 antigen capture assay.

RT aptamers are effective against drug-resistant variants and other HIV subtypes. For the TRTI aptamer to be useful to a wide segment of the global population, it should be effective against a broad spectrum of HIV-1 variants including variants resistant to anti-retrovirals as well as various subtypes of HIV-1. Therefore, cell lines expressing aptamers 70.8,13 (SEQ ID NO:2), 70.15 (SEQ ID NO:3) and 80.55,65 (SEQ ID NO:6) were infected with different drug resistant viruses. For each drug resistant isolate, the aptamers demonstrated drastic inhibition of viral replication, with the aptamer 70.8,13 (SEQ ID NO:2) being consistently the most potent (FIG. 9A). It should be noted that the NNRTI-resistant viruses were most potently inhibited followed by ddI$^r$/ddC$^r$ and PI$^r$ HIV isolates. Thus, the aptamers are effective against variants that can no longer be inhibited by a variety of potent anti-retrovirals.

Figure 9B:
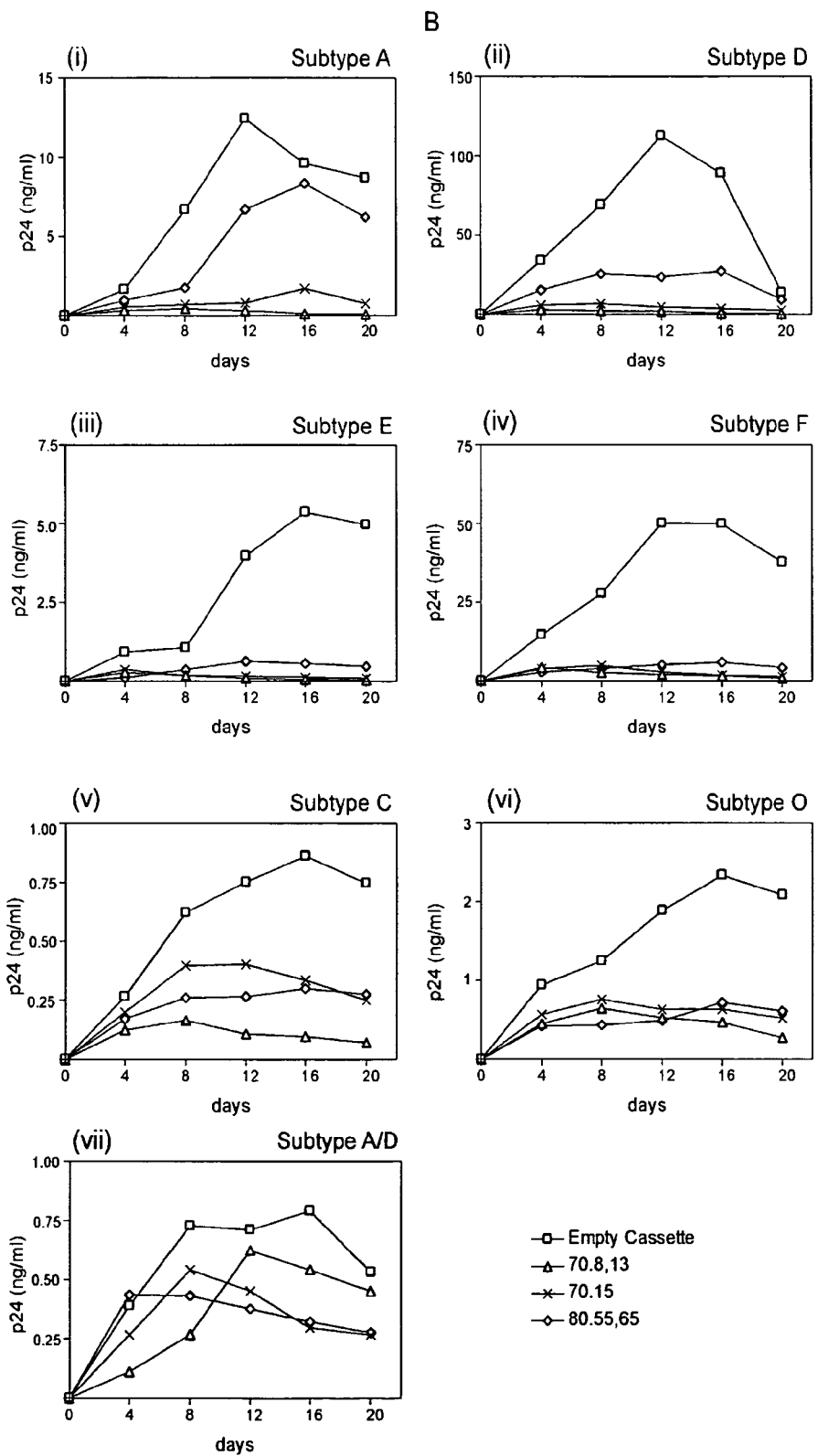

In a similar experiment, seven different subtypes of HIV-1 were used to infect the three strongest aptamer-expressing Jurkat clones and their replication monitored via measurement of p24 in the culture supernatants. The three strongest inhibiting aptamers of subtype B HIV-1 displayed a range of effects that could be broadly grouped into two. One group of viruses belonging to subtypes A, D, E and F were inhibited to a high degree similar to subtype B. Subtypes C, O and the chimeric HIV-1 subtype A/D were moderately or poorly inhibited (FIG. 9B). While these results show that the nature of the pocket that accommodates the aptamer and the template.primer pocket is variable among the subtypes of group M HIVs tested, they clearly demonstrate the potency of the aptamers across a wide spectrum of viral strains and subtypes (FIG. 9B).

Discussion

Although a large number of nucleic acid-based anti-HIV inhibitors have been developed (Konopka et al., 1998; Lee et al., 1994; Michienzi et al., 2000; Sullenger et al., 1990; Symensma et al., 1999) only a few are targeted to RT. These include inhibitors that compete with the template primer (Dirani-Diab et al., 1997; Lu et al., 1997; Westaway et al., 1995), block RT function by irreversibly annealing to the template primer (Lee et al., 1998) and those developed by SELEX to specifically bind to HIV-1 RT (Burke et al., 1996; Schneider et al., 1995; Tuerk and Gold, 1992). While the HIV-1 RT-specific RNA aptamers are known to bind RT (Kensch et al., 2000) strongly their ability to inhibit HIV replication is untested so far. In this report, we have demonstrated the inhibitory capacity of such RNA aptamers when produced in T cells. Analysis of the reverse transcription in HIV-1 infected cells revealed that at least for two of the three best inhibitors, the block in viral kinetics was at an early stage of reverse transcription and the presence of the aptamer prevented the successful elongation of the viral genome. It is known that the unprocessed RT (in Gag-Pol polyprotein) in the budding virus actively recruits tRNA$^{lys,3}$ (Mak et al., 1994). In this report, we demonstrate that it could also sequester the high affinity RNA aptamer. The high affinity aptamers exert a strong influence on viral replication and three of the aptamers severely compromised viral infectivity and the ability of the virus to spread in culture. Furthermore, in the case of the three strongly binding aptamers, there was no emergence of drug-resistant viruses.

The TRTI class of aptamers affords a number of advantages for use as anti-HIV agents. The first advantage is that the use of SELEX for developing anti-RT molecules led to TRTI aptamers with an unprecedented level of specificity and avidity of binding. Since they inhibit HIV-1 RT competitively and are unlikely to inhibit other viral or cellular proteins, they should have little to no toxicity (Burke et al., 1996; Schneider et al., 1995; Tuerk and Gold, 1992). The second advantage is that the expression of aptamers in the infected cell results in encapsidation of the aptamer in the virion particles. Thus, the virions are pre-loaded with an inhibitor that would block the next replication cycle as soon as DNA synthesis would begin. Results of the experiments obtained using a high m.o.i. showed that at the level of expression achieved here, the aptamers were capable of strongly suppressing a 50-to-1 ratio of viruses to cells. The third advantage is that the large interacting interface of the aptamer-binding pocket makes the appearance of resistance mutations a low probability event (Hirao et al., 1998; Tuerk and Gold, 1992). More than one mutation may be required to prevent binding to such a large surface, thus making it less likely an occurrence than single mutations. Furthermore, mutations in an essential binding pocket such as template.primer-binding pocket are likely to render the RT unable to bind its normal template, namely the viral genome. In fact, mutants of HIV-1 RT resistant to DNA aptamers that we isolated in vitro, displayed only low levels of resistance with single mutations (Fisher et al., 2002). Furthermore, the mutations lead to defective processivity in vitro and when placed in the context of a molecular clone of HIV, produced replication-defective viruses. Although this optimism is tempered by HIV's success in developing resistance to every approved drug, one remains hopeful that a drug, which will fail HIV (in terms of developing resistance) will be found.

Intracellular immunization is a powerful approach to inhibit HIV replication and requires introduction, into susceptible cells, of genes encoding for anti-HIV molecules. Thus the development of gene therapy approaches using hematopoietic stem cell therapy for AIDS patients is an active area in multiple laboratories currently (Bai et al., 2001; Bridges et al., 1998; Jayan et al., 2001; Ranga et al., 1998; Woffendin et al., 1996). Use of a therapeutic gene whose product is RNA rather than protein has an added advantage as it prevents the loss of the delivered gene via immune response. When the gene therapy approaches for HIV become available, we speculate that such approaches will be of abundant help in cases of: (i) therapy failures due to anti-retroviral resistance; (ii) for individuals who will need drug holiday due to complications of secondary infections and for (iii) those undergoing structured treatment interruptions (STI).

The extended and efficient intracellular expression of TRTI aptamers via a competent delivery system could lead to powerful alternative drug therapies when combined with the use of enriched hematopoietic stem cells. Prior to their use in humans, one can now attempt hematopoietic stem cell therapy in primates followed by challenge with Simian/Human chimeric immunodeficiency viruses containing HIV-1 RT (Mori et al., 2000).

Example 2

Progress on Anti-HIV RT Aptamers

The results on the effect of anti-RT aptamers reported in Example 1 (published as Joshi et al., 2002) revealed strong inhibition of HIV-1 reverse transcriptase in vitro and during reverse transcription. Of a large number of aptamers tested, three aptamers, 70.8,13; 70.15 and 80.55,65, consistently displayed potent anti-viral activity. These aptamers were initially cloned within two cis-acting ribozymes so that they could be expressed in their native form. The aptamer constructs were driven by a pol II CMV—immediate early promoter and were delivered into cell lines via transfection. In our efforts to further develop our system for aptamer expression and processing, we have accomplished the following additional improvements in expression of the aptamer and its use to inhibit viruses.

Figure 10:
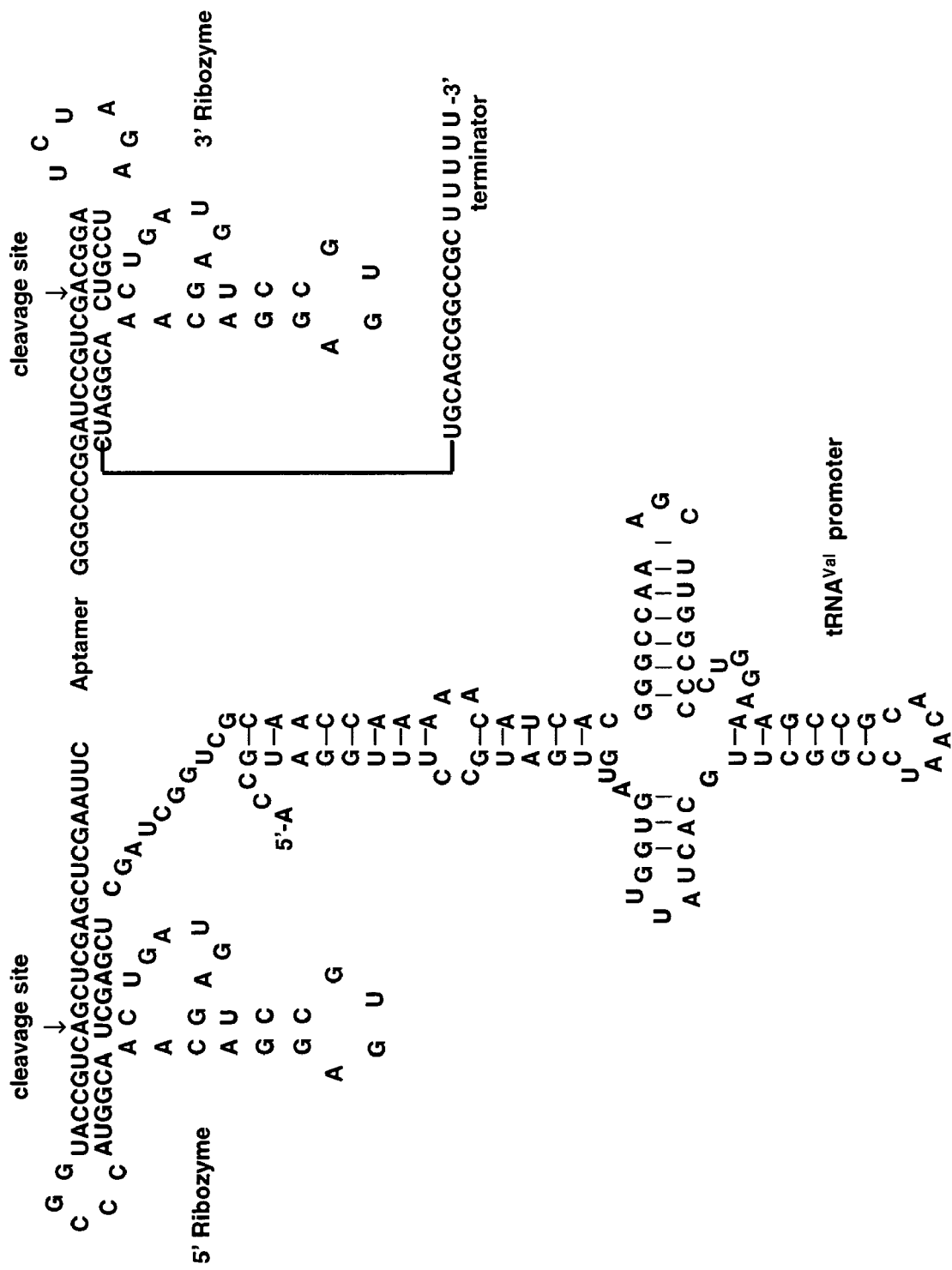
FIG. 10 is a schematic diagram of a representative of a ribozyme-aptamer-ribozyme transcribed by pol III from a tRNA$^{val}$ promoter. Sequences recited in Figure=SEQ ID NO:12 (tRNA$^{Val}$ promoter/5' Ribozyme) and SEQ ID NO:13 (3' Ribozyme/terminator).
Figure 11:
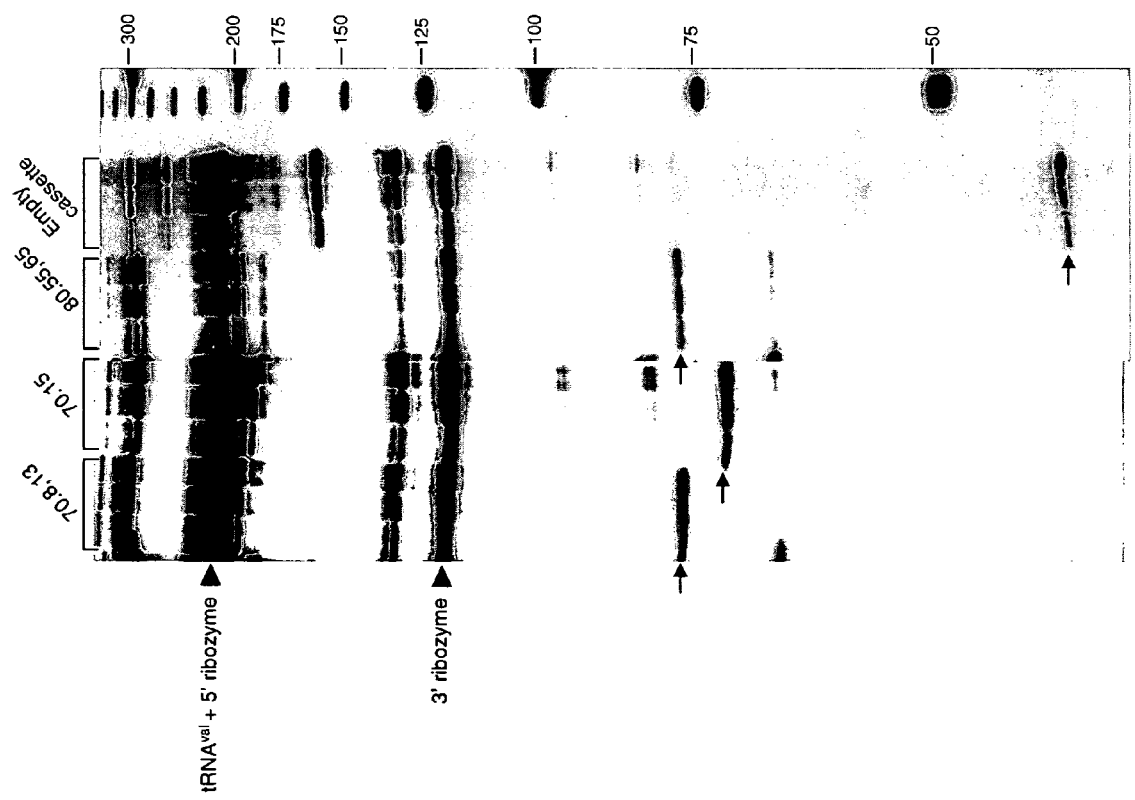
FIG. 11 is an autoradiograph of a denaturing PAGE gel showing the internally radiolabeled products of a T7 in vitro transcription reaction where the transcript includes the tRNA$^{val}$ promoter-ribozyme-aptamer-ribozyme construct of the present invention. The lanes represent three time points of 10 min, 30 min, and 1 hr. The arrows point to the liberated aptamer fragments.

Improvements to the expression system. The aptamer expression system that we have described contained a viral promoter—that of CMV. It is known that viral promoters used in gene therapy are extinguished, making long-term expression impossible. To avoid this problem, we replaced the pol II promoter with a pol III tRNA$^{val}$ promoter, which has been shown to yield high intracellular expression levels (FIG. 10). Further, it has been shown that the transcripts generated from this promoter have a cytoplasmic expression (Kato et al., 2001). The use of a pol III promoter, however, results in the promoter sequences to be part of the transcript as these promoters reside within the transcripts they produce. In vitro transcripts were generated to include the promoter sequences and analyzed on a denaturing polyacrylamide gel to see if the promoter sequences compromised the efficacy of the ribozymes. Analysis of the gel revealed that the additional RNA did not affect the ribozymes and the release of the aptamers suggests that the secondary structure and folding pattern of the transcripts was not altered (FIG. 11).

Figure 12:
FIG. 12 is a diagram of a tRNA$^{val}$ promoter-driven ribozyme aptamer construct cloned into the pBabe MuLV retroviral vector.

Improvements to the vector. The aptamer-expressing cell lines that we used to produce virus particles encapsidating the aptamers (which were then tested for inhibition using reporter cell lines) were generated by transfection of the expression plasmid containing the ribozyme-aptamer-ribozyme construct described in Example 1. It is known that transfection results in the introduction of multiple copies of the aptamer expression plasmid. Thus, the potent inhibition observed could be due to the high copy number of the plasmid. However, typical gene therapy experiments will not lead to multicopy status of the gene introduced. Therefore, we placed the tRNA promoter-ribozyme-aptamer construct into a retroviral vector (FIG. 12). The construct was then transfected into a packaging cell line and the resulting virus particles were used to infect Jurkat cells and CEMx174 cells. Cell lines stably transduced with the aptamer expression construct were selected for puromycin resistance.

Figure 13:
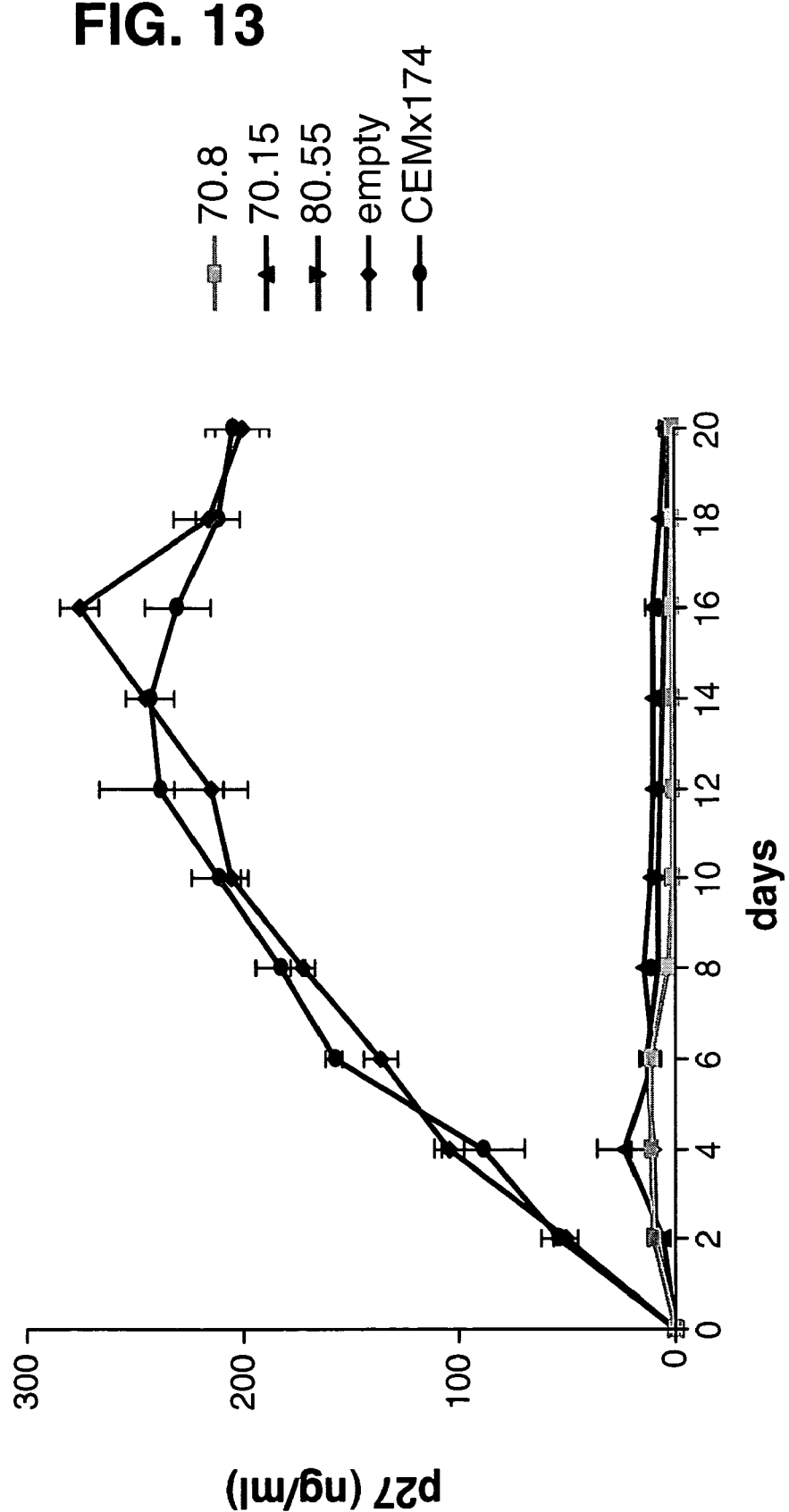
FIG. 13 is a graph of experimental results showing the effective inhibition of SHIV-RT (measured as p27) in CEMx174 cells transduced with anti-HIV RT aptamers 70.8, 70.15 and 80.55 in the vector diagramed in FIG. 12.

Gene therapy protocols prior to being attempted in humans need to be tested in an effective animal model. The SHIV (a recombinant SIV, in which a part of its genome is replaced with the corresponding HIV-1 gene) chimeric viruses are increasingly the preferred viruses to be used. In fact, the efficacy of several NNRTI drugs, which do not inhibit SIV RT, has been tested on monkeys using SHIV-RT viruses (Uberla et al., 1995; Balzarini et al., 1997). Since our aptamer is highly specific to HIV-1 RT, we chose to use SHIV-RT to demonstrate their efficacy in T-cell lines in culture. The CEMx174 cell lines stably transduced with the tRNA promoter driven-ribozyme-aptamer-ribozyme were then infected with SHIV-RT virus which is essentially SIVmac251 in which the RT is replaced with that of HXB2 HIV-1RT (Rosenwirth et al., 2000) at an m.o.i of 1. The aptamers were able to block viral replication in a multi-day cell culture replication experiment (FIG. 13).

Example 3

Aptamers Inhibit HIV-1 Replication More Potently than RNAi

Example Summary

RNA molecules have been shown to be powerful inhibitors of HIV-1 replication. Of the two most prominent RNA molecules, siRNAs and RNA aptamers, which is more potent for blocking HIV is currently not known. In order to determine their relative efficacy, a direct comparison of three anti-HIV aptamers (70.8. 70.15 and 80.55), directed to reverse transcriptase (RT), and three shRNAs targeted to tat, rev and vif regions of the HIV-1R3b genomic RNA was carried out. MMP-eGFP, a murine retroviral vector optimized for expression in hematopoietic stem cells, was used to deliver U6 promoter-driven aptamer RNA or shRNA genes into CEMx174 cells, the transduced cells sorted out via green fluorescent protein function and challenged with HIV. The results show that, at low virus input, shRNAs can inhibit HIV-1 replication as efficiently as aptamers. When expressed in target cells, both classes of inhibitors blocked early events of reverse transcription, suggesting they are both able to access intracellular reverse transcription complexes. However, at higher multiplicities of infection (m.o.i. of 50), that are akin to in vivo onslaught of HIV, the aptamers could efficiently inhibit HIV replication, while shRNAs did not.

RNase protection assays indicated no differences in steady state levels or nucleo-cytoplasmic distribution of these RNAs showing that the differential efficacy was not a reflection of intracellular concentration. The higher potency of anti-RT aptamers appears to be due to their ability to inhibit two successive rounds of reverse transcription owing to their unique ability to be encapsidated into virion particles. Furthermore, anti-RT aptamers expressed in T cells afforded protection against high dose infection by chimeric RT-SHIV viruses.

Introduction

Current therapeutic regimens for HIV-infected individuals are comprised of small molecules that are usually effective in potently suppressing viral titers. However, imperfections in the specificity of the drug can initiate a 'domino' effect, sequentially leading to drug toxicity, poor adherence, viral load rebound and the eventual emergence of resistant variants. Treatment options become progressively limited for individuals who frequently switch drug combinations in response to the changing landscape of resistance mutations. Furthermore, individuals requiring temporary treatment withdrawals would benefit highly from non-toxic regimens that could be used during the interruption.

Although a vigorous search for better drugs is ongoing, a complete absence of toxicity cannot be guaranteed for most small molecule drugs. Among a number of nucleic acid molecules tested as anti-HIV agents, the RNA aptamers warrant special attention. Aptamers display one of the highest degrees of specificity found in biological systems, high-affinity binding and a lack of immunogenicity (Joshi et al., 2003). Aptamers, which are small nucleic acid molecules that bind and inactivate target proteins, are isolated from complex libraries of random sequences of defined length via in vitro selection using specific molecules as binding partners. In recent years, the use of nucleic acid-based therapy in preventive medicine has increased significantly (Joshi et al., 2003). We previously demonstrated that RNA aptamers directed against HIV-1 reverse transcriptase (RT) (Burke et al., 1996), when expressed in CD4+ve T cells, effectively inhibit HIV replication (Joshi & Prasad, 2002). The degree of inhibition directly correlate with in vitro affinity of aptamers to HIV-1 RT. Furthermore, anti-HIV RT aptamers potently inhibited the replication of many drug resistant isolates as well as many different subtypes of HIV-1 (Id).

Another RNA-based approach, the RNA interference (RNAi), using small duplex (siRNA) or small hairpin (shRNA) RNAs has been shown to be effective against HIV-1 (Lee et al., 2002; Novina et al., 2002; Jacque et al. 2002; Coburn & Cullen, 2002; Surabhi & Gaynor, 2002). The siRNAs and shRNAs target specific sites on the mRNA and degrade the target mRNA using cellular machinery. An advantage of RNAi is the use of an intrinsic mechanism to amplify the initial siRNA introduced, and thus is likely to afford potent and durable suppression (Hannon & Rossi, 2004). In order to determine the relative efficacy of aptamers and shRNAs in blocking HIV replication, we delivered selected aptamers or shRNAs directed against HIV-1 of proven efficacy into T-cells using a retroviral vector optimized for expression in hematopoietic stem cells and tested by challenge with HIV-1. Our results show that aptamers directed to HIV RT are more potent antivirals than shRNAs as seen by the greater efficiency at which they suppress early events as well as their effectiveness even at a high multiplicity of infection akin to an in vivo onslaught. The greater efficacy of anti-RT aptamers may be due to a lack of dependence on cellular machinery and their encapsidation into the virion particles, which allows suppression of reverse transcription in two successive rounds of replication.

U6-driven aptamer and shRNA transcripts accumulate at similar levels. We selected three of the most potent anti-HIV RT aptamer RNAs, namely 70.8,13, 70.15 and 80.55,65 (Joshi & Prasad, 2002). For RNA interference, we selected three shRNAs previously reported to be most efficacious in blocking HIV-1 replication. Two shRNAs, T/R1 and T/R2, target the exon 1 and exon 2 of tat/rev genes respectively 4, while a third targets the vif gene (Jacque et al., 2002). For greatest efficacy, both classes of inhibitor RNAs must be present in the cytoplasmic compartment of infected cells. The aptamer RNAs must be present in the cytoplasm to optimally interact with the viral reverse transcriptase in either phase of HIV replication. During early phase, the virion particles disassemble in the cytoplasm, where reverse transcription occurs, while in the late phase of replication, RT as part of Gag-Pol polyprotein precursor, assembles into virion particles in the cytoplasm. Similarly, the viral genomic RNA, the target of the shRNAs, must transit through the cytoplasm both during viral egress from producer cells and entry into target cells. We selected Pol III promoter of U6 RNA for the expression of both aptamers and shRNAs since U6-derived promoters result in high-level expression and the shRNAs expressed from U6 promoter localize to the cytoplasm (Kawasaki & Taira, 2003; Li et al., 2003; Paul et al., 2003; Boden et al. 2003).

Figure 14:
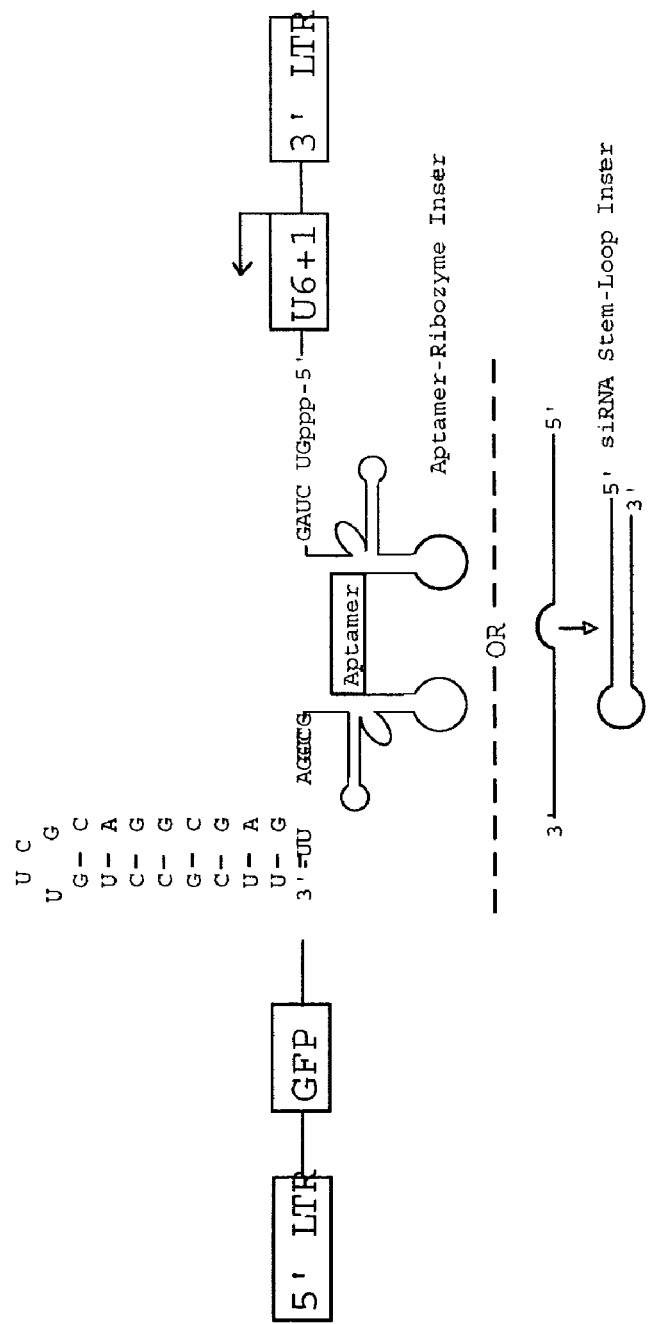
FIG. 14 is a diagram of MMP-eGFP. The ribozyme-aptamer-ribozyme and shRNA cassettes were cloned downstream of the U6+1 promoter and followed by a short stem loop sequence and a run of U's, which served as the pol III transcription terminator. The entire expression cassette was introduced into the MMP-eGFP retroviral transfer vector in the reverse orientation. Sequences recited in Figure=SEQ ID NO:14 (5' connector sequence) and SEQ ID NO:15 (3' connector sequence).
Figure 15:
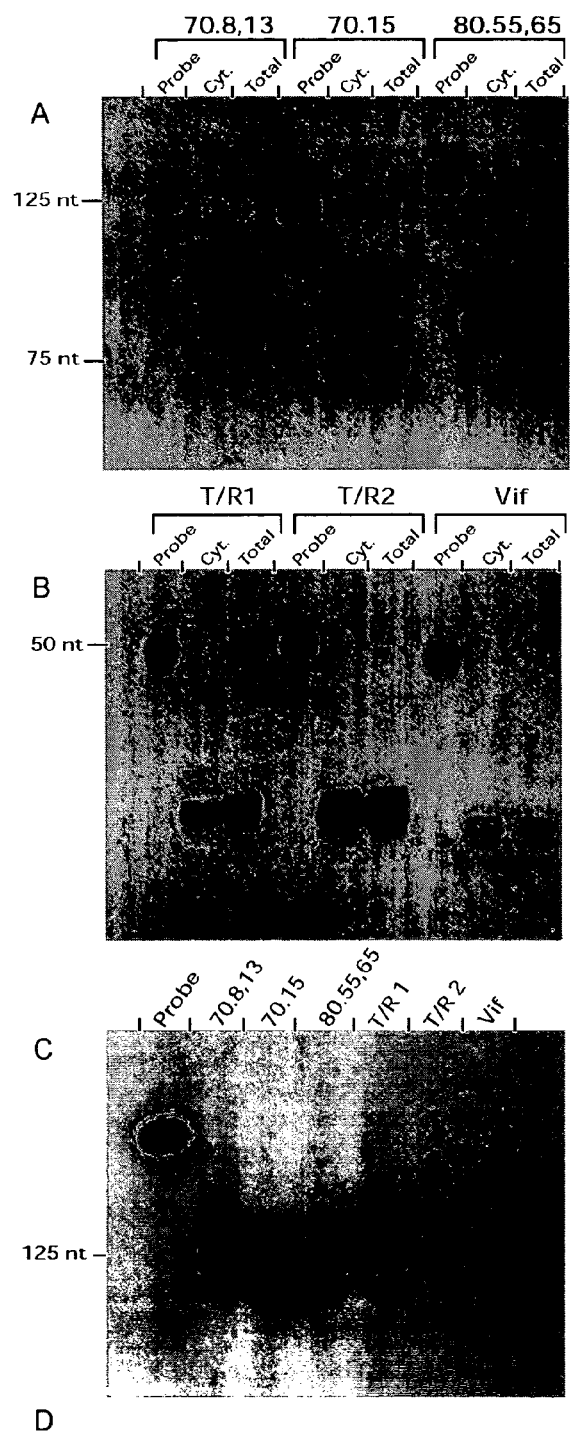
FIG. 15 is autoradiographs and a table of RPA analysis of the aptamer and shRNA levels in CEMx174 cells. Panel A shows cytoplasmic and total RNA isolated from CEMx174 cells transduced with MMP-eGFP containing each of the aptamer sequences was hybridized to [$^{32}$P]-labeled anti-sense RNA. Subsequently, the hybrids were digested with a cocktail of RNase A and RNase T1 and the protected fragments resolved on a 10% polyacylamide gel. Gels were dried and exposed to a phosphorimager screen for quantitative densitometric analysis of expression levels. Panel B shows the same analysis as performed on cells transduced with each of the shRNA-containing retroviral vectors. Panel C shows total RNA from the aptamer- and shRNA-expressing CEMx174 cell lines probed for the β-actin gene. Panel D shows, the percent of total present in the cytoplasmic fraction or the total or aptamer- or shRNA-expressing cells as a percent of the β-actin mRNA.

We used the MMP-eGFP retroviral vector containing a chimeric LTR-derived from Murine myeloproliferative Sarcoma Virus (MPMV) and Murine Leukemia Virus (MULV) sequences (Riviere et al., 1995), which has been successfully used to transduce Rhesus CD34+ hematopoietic stem cells (Rosenzweig et al., 2001). The aptamer RNAs were inserted along with flanking, self-cleaving ribozymes, which cleave the sequences abutting the aptamer to minimize misfolding (Joshi & Prasad, 2002). The shRNA transcripts were made with a short stem-loop between the two self-complementary segments followed by a U6 transcription termination site as described by Paul et al. (2003) (FIG. 14). In order to prevent reductions in viral titer caused by premature processing of the retroviral RNA transcript, the entire U6 promoter-aptamer/shRNA cassette was placed in the opposite orientation downstream of the GFP coding sequence. CEMx174 cells were infected with retrovirus stocks of MMP-eGFP carrying each of the three aptamers and three shRNAs, followed by isolation of transductants by sorting for GFP+ cells. After limiting dilution plating of transductants followed by expansion, RNase Protection Assay (RPA) analysis of total and cytoplasmic RNA were performed. The RPA analysis revealed abundant expression of the aptamer RNAs and shRNAs in the cytoplasmic fraction (FIG. 15). Approximately 52 to 85% of the total U6 expressed aptamer and shRNA transcripts were present in the cytoplasm. In addition, when quantitatively compared with β-actin, the U6 transcribed RNAs were between 24 to 42% of β-actin.

Figure 16:
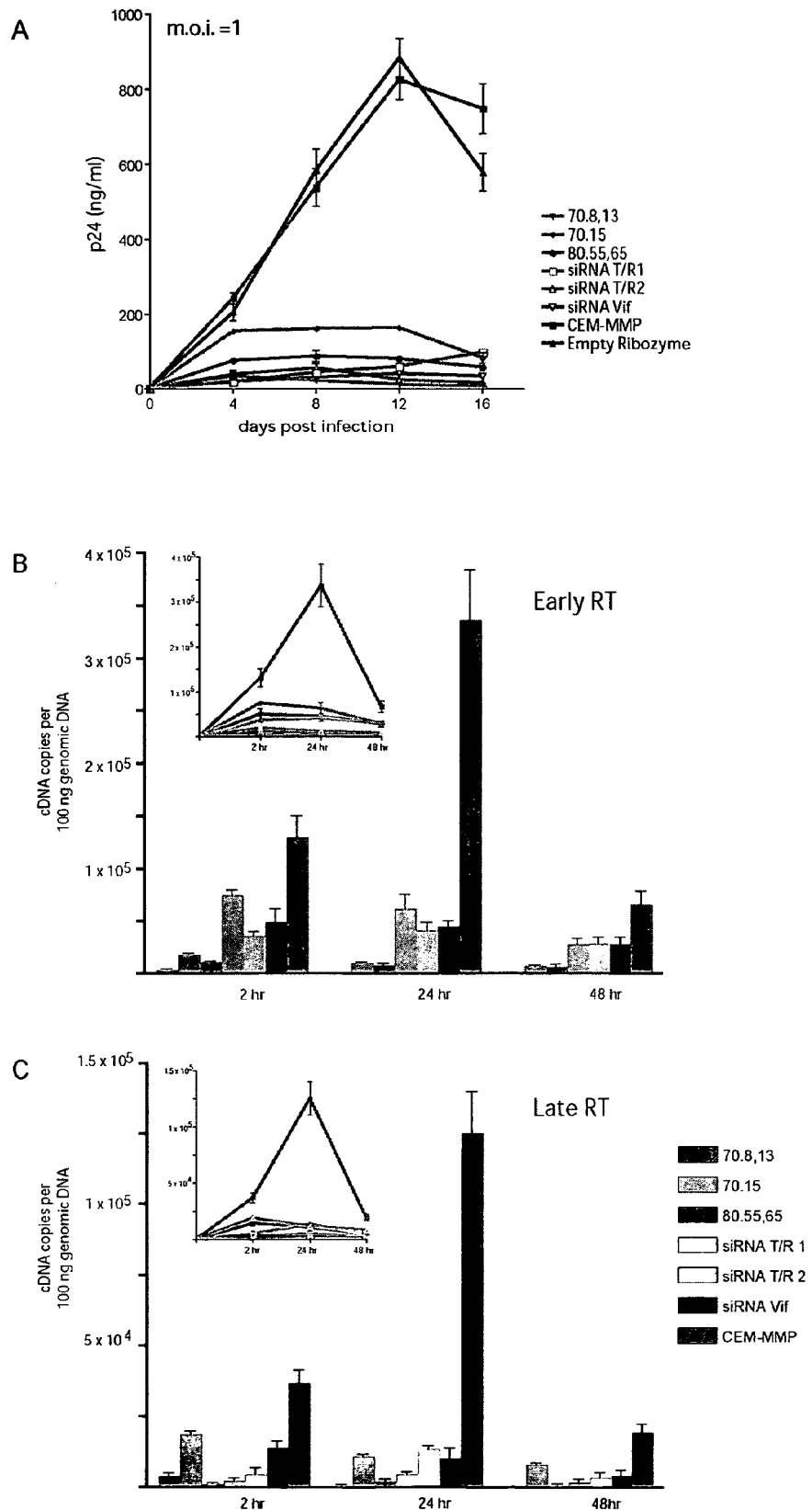
FIG. 16 is graphs of experimental results showing inhibition of HIV-1 replication by anti-RT aptamers and shRNAs at low multiplicity of infection. Panel A shows a comparison of inhibitory effects of aptamers and shRNAs. CEMx174 cells stably expressing anti-viral RNA were infected with HIV-1 at an m.o.i. of 1 and culture supernatant assayed for p24 antigen production every 4 days. Results are expressed as a mean±SD of three separate infections. Panels B & C show Real Time PCR of early and late products of viral reverse transcription. Transduced CEMx174 cells were infected with HIV-1 at an m.o.i. of 1 and at set time points, cells were harvested and total genomic DNA extracted. The DNA was then subjected to PCR amplification with primers and probes specific for the early and late products of proviral synthesis (Julias et al., 2001; Butler et al., 2001). Results are expressed as a mean±SD of two separate infections and represented as a bar graph and continuous line graph (inset).

Aptamers and shRNAs can both potently block early events. The anti-viral effects of anti-RT aptamers and shRNAs were tested using pools of transduced CEMx174 cells. We challenged GFP+ CEMx174 cells with HIV-1$_{R3b}$ at an m.o.i. of 1 and monitored virus production for 16 days in culture by p24 ELISA. Both classes of antiviral RNAs blocked viral replication (FIG. 16A). Although shRNAs appeared to be generally more effective in suppressing HIV replication, the aptamer 70.8,13 displayed the strongest anti-HIV phenotype (FIG. 16A).

Figure 17:
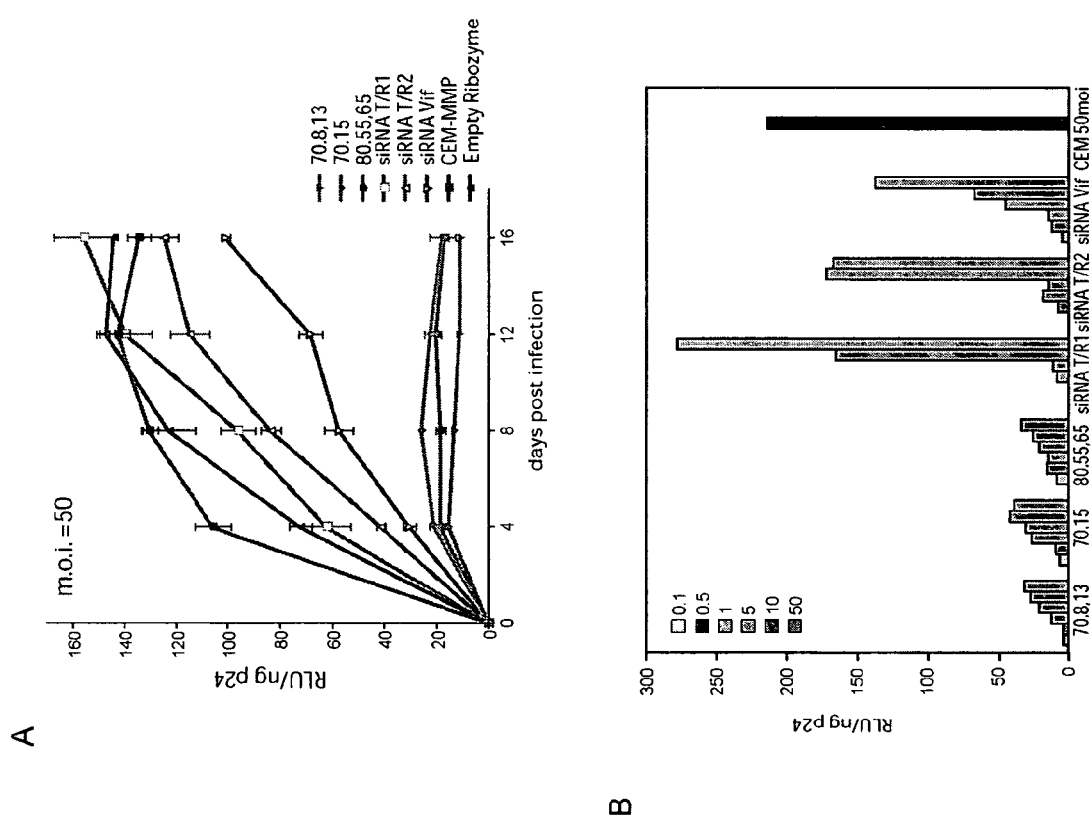
FIG. 17 is graphs of experimental results showing the effect of virus input on the degree of inhibition by aptamers and shRNAs. Panel A shows viral growth kinetics at an m.o.i. of 50. The aptamer and shRNA-expressing cell lines were infected with HIV-1R3b at a m.o.i. of 50. Culture supernatant was collected every four days to determine both p24 levels and infectivity using LuSIV luciferase reporter cells. Results obtained from that analysis are expressed as RLU per ng p24 in the medium. Panel B shows the effects of titrating the virus input to determine the maximum sustainable inhibition. Transduced CEMx174 cells were infected with HIV-1 at m.o.i.'s ranging from 0.1 to 50 and cultured for 16 days. Supernatant was used to infect LuSIV cells and the RLU determined from the cell lysate. Control CEMx174 cells were infected at an m.o.i of 50 and results are expressed as RLU per ng of p24 in the medium at day 16.

Some, but not all, siRNAs have been shown to inhibit early events in HIV infection by targeting the viral RNA genome that templates reverse transcription (Lee & Rossi, 2004). It has been argued that the variable ability of siRNAs to block reverse transcription is due to the differential accessibility of the viral genomic RNA contained within the newly uncoated virus nucleocapsid (Hu et al., 2004). Thus, we compared the relative ability of aptamers and shRNAs to block reverse transcription in HIV-1 infected cells. CEMx174 cells expressing each of the aptamers and shRNA molecules were infected with HIV-1 at an m.o.i. of 1, the cellular DNA isolated from infected cells (at 2 h, 24 h and 48 h post infection) and the early and late intermediates of reverse transcription quantified via real time PCR (FIG. 16B). At 2 and 24 h post infection, the formation of early intermediates of viral cDNA synthesis was inhibited by 86-96% and 98-99% in the aptamer-expressing cells and 43-62% and 82-90% in shRNA-expressing cells respectively. While both aptamers and shRNAs blocked the formation of minus strand strong stop DNA, the first observable product of reverse transcription, the inhibition was more rapid and stronger with aptamer RNAs. The pattern of inhibition of the late cDNA products was similar to that of early products, although the difference between the aptamers and shRNAs was less marked (FIG. 16C). Nevertheless, our results suggest that shRNAs bind to viral RNA present within a nucleoprotein complex and signal its degradation. Our results also suggest that aptamer RNAs penetrate RTCs, bind and inhibit RT. This effect is more pronounced at the 24 h time point where virtually no products of early transcription events are observed in the presence of aptamers. Thus, aptamers can overcome the variation in accessibility of the genome sites by directly targeting the polymerizing enzyme.

shRNAs are inefficient at blocking HIV at high multiplicities of infection. Studies testing the efficacy of siRNAs against HIV tend to employ a very low inoculum of HIV (with m.o.i. being generally in the range of 0.001 to 0.1), thus creating conditions that are artificially favorable to siRNA inhibition. Efficacies of shRNAs at high inocula have not been tested. Therefore, we compared the ability of intracellular aptamers and shRNAs to inhibit a high multiplicity of infection. In an experiment similar to that depicted in FIG. 16A, we challenged clonal CEMx174 cells expressing each of the six anti-HIV RNAs with HIV-1 at an m.o.i. of 50 and monitored virus production over 16 days. Our results were striking in that the aptamers retained a strong suppression of HIV even at high virus input, while shRNAs displayed mild to no effect. At this virus input, the levels of HIV replication in cells expressing shRNAs approached that of the negative controls which expressed either a U6-ribozyme construct without any anti-HIV sequences or the plain, untransduced CEMx174 cells (FIG. 17A).

The apparent failure of the shRNAs to inhibit viral replication at high inoculum was surprising in view of the fact that shRNA effect is known to be amplified by the cellular RNAi pathway, which should result in a strong anti-viral response. Therefore, we performed additional virus titration experiments to determine the range of virus input levels at which the RNAi remains effective relative to that for aptamers. Cells stably expressing aptamers or shRNAs were infected with HIV-1 at an increasing m.o.i. ranging from 0.1 to 50. The supernatant was collected after two weeks of continuous culture and the virus released was quantified using LuSIV reporter cells (FIG. 17B). Our results reveal that aptamers retain their inhibitory effect at all virus input levels, although the inhibition was progressively reduced with increasing m.o.i.s. On the other hand, the shRNAs were effective only up to an m.o.i. of 5. Consistent with the data in FIG. 17B, there was very little or no inhibition at 10 or 50 m.o.i. The anti-vif shRNA retained the highest inhibitory effect with close to 70% inhibition even when infected at an m.o.i. of 10, while the other two shRNAs, directed to Tat/Rev exons were virtually ineffective at this and higher virus inputs. Alignment of shRNA sequences with the corresponding regions of the HIV-1R3b did not reveal any mismatches indicating that the differences are not due to incomplete hybrid formation. These results corroborate the view that the siRNAs are highly effective in blocking viral replication only at lower doses of infection, but cannot rival the inhibitory potential of the aptamers at high virus inputs. When the cells encounter an in vivo-like onslaught of virus particles, the siRNA mechanism is ineffective at neutralizing the virus.

Figure 18:
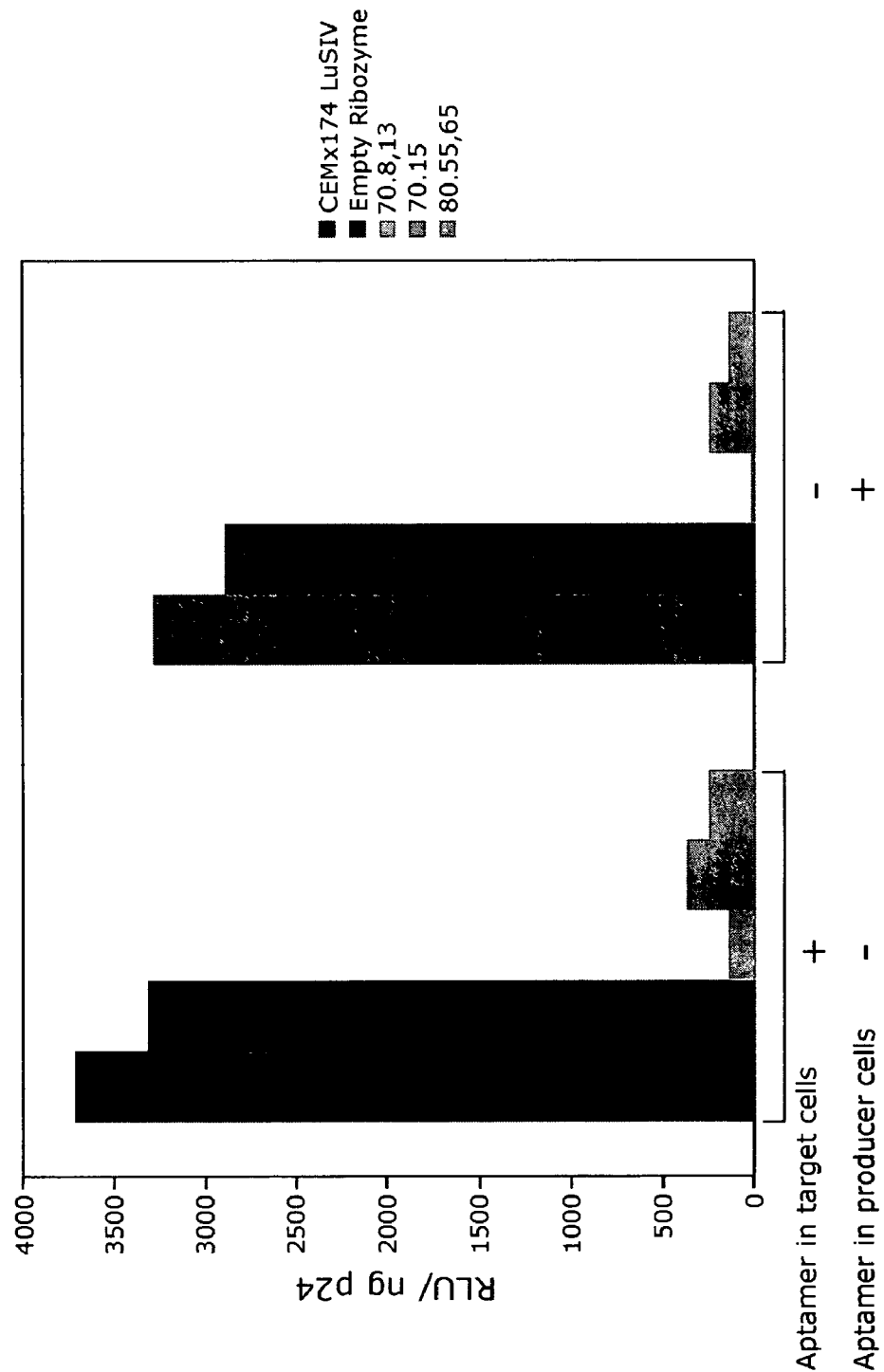
FIG. 18 is a graph of experimental results showing that aptamers can block infection when expressed in recipient cells or in producer cells. Reporter LuSIV cells transduced with aptamer-expression cassette (left panel) or plain LuSIV cells (right panel) were infected with HIV-1 produced either in parental 293T (40 ng p24; left panel) or the aptamer-expressing 293T (10 ng p24; right panel) cells. Cell lysates were analyzed for luciferase activity 24 hrs post infection.

Aptamers can act at two successive rounds of reverse transcription. Next, we used single cycle infection experiments to investigate the basis for the superior inhibitory effect of aptamers over shRNAs. We previously showed that virion particles produced from cell lines expressing aptamers were blocked for reverse transcription in a subsequent round of infection in Jurkat T cells (Joshi & Prasad, 2002). Our results in FIG. 16B show the ability of aptamers, when expressed in the recipient cells, to penetrate the RTC and block reverse transcription. We wanted to compare, side-by-side, the effects of aptamer brought from the virion producer cells via encapsidation vs. that of the aptamer expressed in the recipient cells. We transduced CEMx174 LuSIV, a reporter cell line containing a HIV-1 Tat-responsive luciferase gene with the ribozyme-aptamer cassettes. We used either parental LuSIV cells or LuSIV cells transduced with the aptamer construct for infection. These cells were infected, at an m.o.i. of 1, with HIV-1 produced from 293T cells either expressing or not expressing an aptamer. After 24 hours, the infected cells were lysed and the lysates assayed for luciferase activity (FIG. 18). The results demonstrate that similar suppression is achieved irrespective of whether the aptamer is expressed in the producer cells or in the recipient cells. The results suggest that once the virus encounters a cell expressing an aptamer, it is subject to inhibition at two successive rounds of reverse transcription. In other words, even if the incoming virus escapes the block to reverse transcription and proceeds to complete the infectious cycle, the progeny virions released will have encapsidated aptamers. When such virus particles infect the next recipient cell, even if that cell lacks aptamers, the aptamer in the virion would still block reverse transcription. This dual effect may be responsible for the ability of aptamers to block infection at high m.o.i.

Figure 19:
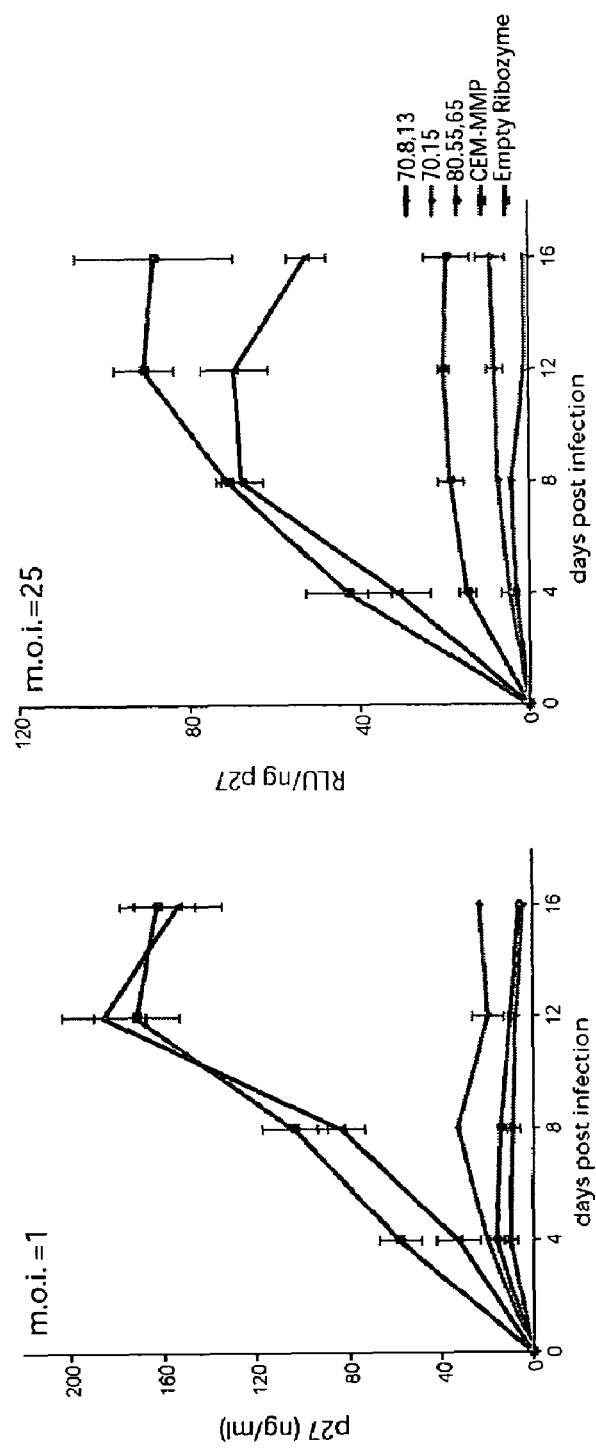
FIG. 19 is graphs of experimental results showing the effect of aptamers on the replication kinetics of chimeric RT-SHIV viruses. CEMx174 cells stably transduced with each of the aptamer-expressing MMP-eGFP viruses or control cells that were transduced with either the parental MMP-eGFP virus or the MMP-eGFP containing the ribozyme cassette without any aptamer sequences, were infected with RT-SHIV at a low (m.o.i.=1; left panel) and high (m.o.i.=25; right panel) infectious dose. Viral production was monitored over a period of 16 days and the supernatant collected every 4 days and assayed for p27 production and infectivity using the luciferase reporter cell line. In the left panel, which shows the inhibitory effect of aptamers at low dose infection, the values plotted on the y axis represent p27/ml of medium, while on the right panel, which depicts the effect at high dose infection, the y axis values represent ratio of infectivity as RLU/ng p27. This was due to the fact that at low m.o.i., the levels of RLU was barely detectable.

Anti-HIV-1 RT aptamers block RT-SHIV replication in cell culture. Our ultimate goal is to evolve the aptamers from bench studies to the clinic to benefit infected individuals. This requires extensive efficacy tests in a primate model. An ideal primate model for such testing would involve macaques infected with recombinant RT-SHIV viruses, in which the SIV RT is replaced by HIV RT (Uberla et al., 1995). Although the aptamers were developed specifically to interact with HIV-1 RT, it is possible that they might not react with similar dynamics against a recombinant RT-SHIV virus. Therefore, CEMx174 cells stably expressing aptamers were exposed to RT-SHIV at low (m.o.i.=1) and high (m.o.i.=25) infectivity doses and the viral growth kinetics monitored in a continuous culture system. Our results show that the aptamers limit the spread of RT-SHIV at both doses tested (FIG. 19). The degree of inhibition observed is very similar to that observed with HIV-1$_{R3b}$ (compare FIG. 19 with FIGS. 16A and 17A). These observations set the stage for future studies aimed at evaluating the efficacy of aptamers using the macaque-RT-SHIV model.

Discussion

In this report, we have described pre-clinical efforts to develop the aptamer approach as a viable, alternative or complementary therapy to the standard HAART protocols. The U6 promoter we employed ensured a high level of expression of the aptamer RNAs in the cytoplasm, the site where reverse transcriptase, the target of the aptamers, is synthesized and performs its function. Any anti-HIV RNAs will need to be expressed in hematopoietic cells and gene delivery via retroviral vectors into such cells places a number of limitations. First, the approach used here requires a vector that is ideally suited to hematopoietic cells. Therefore, we have employed MMP-eGFP, a modified MuLV retroviral vector that is optimized for expression in such cells. Second, retroviral vectors containing self-cleaving ribozymes can result in reduction in the titer due to cleavage of the viral RNA genome during virus production. We have addressed this by expressing the U6-driven aptamer transcript in an orientation that is opposite to that of the LTR-driven expression. Third, selection of transductants via drug markers can negatively affect the viability of transduced cells. Thus, we have used GFP expression as a marker of transduction and used flow cytometry to enrich for transduced cells. Further knowledge about whether GFP expression will affect the survival or differentiation of hematopoietic stem cells will help design future vectors for use in vivo.

Although our studies used CEMx174 cell lines, the methods used here are also applicable to primary hematopoietic cells. Since the site of integration of the retroviral vector determines expression levels, a population of transduced cells will display a range of expression levels. It is reassuring that both clonally expanded transductants (FIG. 16A) and pools of transduced cells are equally able to block HIV infection (data not shown).

We have made several important observations that lend support to the fact that aptamers may be superior to RNAi in potently blocking HIV. First, when tested under low infectious doses, the aptamer RNAs and the shRNAs both appear to be equally efficacious. The observed inhibition of strong stop DNA formation by shRNAs is presumably mediated by the degradation of viral RNA genome, which must occur before the initiation of reverse transcription. The shRNAs must attract the silencing apparatus to the vicinity of RTC resulting in target degradation. It is surprising to see that the shRNAs used here, whose targets lie multiple kilobases away from the site of initiation of reverse transcription, are able to induce the degradation of primer-binding site (pbs) sequence as shown by the inhibition of this earliest event (FIG. 16B, 'Early RT' panel) However, the aptamer RNAs appear to be even more rapid and efficient in exerting their inhibitory effect on the formation of early RT products. For example, the aptamers bring about 86-96% inhibition of early RT products as early as 2 hours after infection (FIG. 16B, 'Early RT' panel), whereas the shRNAs, on average resulted in about 42-62% inhibition of the same early RT products (FIG. 16B). Previous reports have suggested that the inhibition of the early events by shRNAs is variable and dependent on the target sequence, implying that accessibility of shRNA targets is not uniform (Lee & Rossi, 2004; Hu et al., 2004). Anti-HIV RT aptamers, on the other hand, eliminate this problem by directly targeting the viral RT and blocking its function. Although detailed investigations into RTCs have recently begun (Fassati & Goff, 2001), currently not much information is known about RTCs in HIV-infected cells. Reverse transcription takes place within a nucleoprotein complex that consists of the genome, HIV-1 RT, IN, nucleocapsid (NC) and Vpr proteins (Bukrinsky et al., 1993). However, information about the accessibility of the genome or the polymerase in these RTCs to anti-viral nucleic acids that must directly interact with them is currently minimal. For the first time, our results show that aptamers and shRNAs expressed in recipient cells can penetrate the intracellular RTCs to bind the genome or the polymerase.

Second, aptamers severely compromised viral growth kinetics at all doses tested. In contrast, the shRNAs inhibited viral replication more potently only when challenged with lower doses of HIV and their efficacy waned when exposed to saturating amounts of virus. While the shRNA phenomenon has been shown to be a successful means of viral gene silencing, it appears that the anti-viral effects are observed only in the presence of lower ratios of virus-to-cell. This is most likely due to the fact that the silencing phenotype requires a concerted chain of events including multiple cellular components in order to create the desired effect (Stevenson, 2003) as opposed to the aptamers that manifest their inhibition autonomously.

Third, our results suggest that the superior efficacy of aptamers may be due to their ability to act at two successive cycles of reverse transcription. We have shown that inhibition by aptamers can occur at two levels, the first mediated by aptamers invading the incoming virion complex and the second by the aptamer itself being encapsidated into virions that escape the first step above (FIG. 18). In other words, if any virus escapes inhibition, it could still be blocked at the next infectious cycle.

It has been shown that resistance to siRNAs can be generated with ease (Boden et al., 2003; Das et al., 2004). In contrast, resistance to aptamers is likely to be difficult due to the large interaction interface. Using aptamer-expressing cells, we have attempted to generate resistant viruses by selection in vitro, but with no success so far. Furthermore, we previously isolated two aptamer-resistant RT mutants using a phenotypic screen that led to two mutations adjacent to the minor groove-binding track in the thumb subdomain (Fisher et al., 2002). Each of these mutants displayed only low-grade biochemical resistance in vitro. When the mutant RT sequences were incorporated into replication competent molecular clones of HIV, the resulting viruses were severely compromised for infectivity. Our extensive biochemical analyses showed that the mutations target functionally critical residues that are involved in template:primer recognition. Thus, aptamer-resistant variants are unlikely to arise both due to the severity of viral suppression achieved by aptamers as well as the fitness penalty imposed by the resistance mutations.

Methods

Plasmids and vectors. The three ribozyme-aptamer cassettes (70.8,13; 70.15; and 80.55,5) along with the empty ribozyme cassettes were excised from the pcDNA 3.1 clones prepared previously (Joshi & Prasad, 2002). The T/R1 & T/R2 shRNA and the vif shRNA sequences were as described by Lee et al. (2002) and Jacque et al. (2002) respectively. Since the RNA constructs were to be expressed as a single transcript, each of the shRNAs included a 9 nt loop linker sequence between the complementary strands which was derived from Castanotto et al. (2002). The shRNA cassettes were generated by annealing gel purified complementary oligonucleotides with specific cloning overhangs and then directionally inserted downstream of the U6 promoter.

The U6 promoter sequence was PCR amplified from the plasmid pTZ U6+1 (kindly provided by Dr. John Rossi) and cloned into pBluescript KS+ (Stratagene, Calif.) to generate pBKS+U6. During amplification, the XbaI and EagI cloning sites were introduced between the pol III promoter and the terminator sequence to aid in cloning. The shRNA and ribozyme-aptamer constructs were first cloned into the intermediate pBKS+U6 where the orientation and sequence integrity were confirmed by DNA sequencing. The entire expression cassette was then cloned, in reverse orientation, downstream of the GFP reporter into the MMP-eGFP retroviral transfer vector (obtained from Dr. Richard Mulligan, Gene Therapy Initiative, Harvard Institute of Human Genetics) (Riviere et al., 1995).

Cell lines and viruses. The Phoenix amphotropic retroviral packaging cell line was purchased from the American Type Culture Collection. The CEMx174 and P4/CCR5 cell lines used in this study were obtained from the NIH AIDS Reference and Research Reagent Program. The CEMx174 LuSIV luciferase reporter cell line was kindly provided by Dr. Janice Clements (Roos et al., 2000). CEMx174 cells, which are permissive to both HIV-1 and SIV, were grown in RPMI 1640 (Invitrogen, Carlsbad, Calif.), supplemented with 10% fetal bovine serum (FBS) (Invitrogen, Carlsbad, Calif.), 100 U/ml penicillin, 0.1 mg/ml streptomycin. All cells were maintained at 37° C. in a humidified 5% $CO_2$ atmosphere.

Infectious HIV-1R3B virus stock was prepared by transfection of the R3B molecular clone into 293T cells. The culture supernatant was collected 36-48 hours post-transfection and the viral infectivity units calculated using the P4/CCR5 β-galactosidase reporter cell line and the viral titer determined using a commercially available p24 ELISA kit (Perkin Elmer, Boston, Mass.). Titered viral stocks were stored at −80° C. buffered with 10 mM HEPES.

Stocks of RT-SHIV and SIVmac239 were prepared from the appropriate 5'- and 3'-half clones (containing a nef orf), as described previously (Giuffre et al., 2003). The 5'-half clone of the RT-SHIV, containing the RT-encoding region from HIV-1 HXBc2 18 was provided by Dr. Joseph Sodroski (Harvard Medical School, Boston, Mass.). Stocks of RT-SHIV were prepared following transfection of appropriate clones into CEMx174 cells by electroporation, as previously described (Murry et al., 2003). Virus stocks were prepared from culture supernatants of infected CEMx174 cells. Cells were removed from the culture medium by centrifugation at 600×g for 5 min. Aliquots of supernatants were stored frozen at −80° C. The RT-SHIV stocks used for these studies had the T to C substitution at position 8 of the SIV tRNA primer binding site, which is necessary for rapid replication of RT-SHIV in vivo (Soderberg et al. 2002). These stocks were thawed and used to infect cells for subsequent studies.

Transduction of CEMx174 cells. The CEMx174 cell line was used to generate aptamer and shRNA-expressing target cells since they can be infected with both HIV-1 and SHIV. The Phoenix amphotropic packaging cells were plated at 30-40% confluence in DMEM supplemented with 10% FBS and transfected with 10 μg of the recombinant transfer MMP-eGFP vector using the GENE PORTER (San Diego, Calif.) lipofection procedure. Twelve to fourteen hours post-transfection, the medium was replenished and the supernatant collected 36-48 h later. The viral supernatant was titrated on NIH 3T3 cells and used to transduce $1 \times 10^5$ CEMx174 cells at a low m.o.i of 1 in a final volume of 2 ml RPMI 1640 with 10% FBS. Two hours after infection, the cells were collected by centrifugation and resuspended in 10 ml of fresh growth medium as above and were allowed to expand for 48-72 h or until the cells expressed eGFP. The cells were then sorted using a fluorescence activated cell sorter (FACStar Plus, Beckton Dickinson, Franklin Lakes, N.J.) and $10^3$-$10^4$ eGFP positive cells were either pooled or expanded as individual clones after limiting dilution plating. Control GFP-expressing stable cell lines were also created in a similar fashion using the parental MMP-eGFP transfer vector.

RPA analysis. Intracellular levels of both aptamer RNAs and shRNAs in the transduced eGFP positive CEMx174 cells was measured using the mirVANA™ mRNA detection kit (Ambion, Austin, Tex.). Briefly, total RNA was extracted from transduced recombinant cell lines using the TRIZOL reagent (Invitrogen, Carlsbad, Calif.). Cytoplasmic RNA was extracted by washing cells in cold PBS followed by the addition of a mild lysis buffer containing 50 mM Tris.Cl pH 8.0, 100 mM NaCl, 1 mM $MgCl_2$, 0.5% (v/v) N-lauroylsarcosine, 1 mM DTT and 1000 U/ml RNase inhibitor and incubated at 4° C. for 10 minutes. The cell lysate was then centrifuged at 4° C. for 5 minutes, an equal volume of TRIZOL reagent added to the supernatant collected and the cytoplasmic RNA extracted as per the manufacturer's instructions. The RPA was performed using antisense RNA synthesized as run off transcripts from a T7 promoter and the radiolabeled probes were gel purified on a 10% polyacrylamide gel and quantitated via scintillation counting. Approximately $1 \times 10^4$ cpm of probe was used to hybridize to equivalent amounts of total and cytoplasmic RNA and the reaction was carried out overnight at 42° C. A proprietary mixture of RNase A and T1 was used to digest the non-complimentary strand and the protected probe fragments were then resolved on a 10% denaturing polyacrylamide gel. Intracellular levels were then compared with an internal control of β-actin using a phosphorimager (STORM 820, Molecular Dynamics).

Virus challenge assays. The antiviral efficacies of the aptamers and the shRNAs against HIV were tested in vitro by infecting the transduced CEMx174 cells with infectious HIV-1 or SHIV at variable m.o.i. as follows. The stably transduced cell lines were expanded and $1 \times 10^5$ viable cells were then infected with the respective viruses at the desired m.o.i. Infection was carried out in a total volume of 2 ml of growth medium for 2 hours and then cells were washed twice in PBS. The infected cells were resuspended in 10 ml of growth medium and cultured for up to 18 days while 100 μl samples of supernatant were collected at 4 day intervals for the p24 or p27 antigen capture assay (Perkin Elmer, Boston, Mass. and Coulter, Miami, Fla. respectively). In addition, 100 μl samples were also collected every 4 days and used to infect $1 \times 10^5$ CEMx174 LuSIV cells. Cells were harvested 24 hours post-infection and the luciferase activity in the cell lysate measured (Promega, Madison, Wis.). The relative luciferase units (RLU) detected were normalized to the amount of input virus based on the p24 or p27 antigen assay values and the calculated results are expressed as RLU per ng p24/p27 of infecting virus.

Quantitative real-time PCR. Supernatants of infectious HIV-1 virus stock obtained from the transfection of 293 cells were passed through a 0.45-μm filter and treated with 50 U/ml of DNase I (Roche, Indianapolis, Ind.) for 1 hour at 37° C. Treated virus supernatant was then used at an m.o.i of 1 to infect ($3 \times 10^5$) the aptamer and shRNA expressing CEMx174 cell lines. Two hours post infection, the cells were washed in PBS, one aliquot was used for DNA extraction and rest were cultured for an additional 24 and 48 h in complete growth medium. The total genomic DNA was extracted at the end of each time point using the DNeasy Tissue kit (QIAGEN, CA). The extent of proviral DNA synthesis was quantitated using the RU5 primers and probe set (Julias et al., 2001) for the early HIV-1 reverse transcripts and the MH531 and MH532 primers and the LRT-P probe (Butler et al., 2001) for the late HIV-1 reverse transcripts as described. Reaction mixtures included the TaqMan universal master mix (Perkin-Elmer, Foster City, Calif.), 200 nM primers and probe for the early RT products and 300 nM primers and 100 nM probe for the late RT products and 100 ng of genomic DNA. The PCR conditions were 2 min at 50° C., 10 min at 95° C., followed by 40 cycles of 15 sec at 95° C. and 1 min at 60° C. run on an ABI Prism 7700 sequence detection system (PE-Applied Biosystems, Foster City, Calif.).

In view of the above, it will be seen that the several advantages of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

SEQ ID NO's. For Aptamer sequences, the extraneous flanking sequences are in bold.

SEQ ID NO: 1
Aptamer 1.1
AGCTCGAGCTCGAATTCGGGAGATTCCGTTTTGAGTCCGGGAAAAACTGAAGGGCCCGGATCCGTC

SEQ ID NO: 2
Aptamer 70.8,13
AGCTCGAGCTCGAATTCAAAGAGATCTGGCAGTGTCACAACCAGGAAAAAGACACGACGAAC GGGCCCGGATCCGTC

SEQ ID NO: 3
Aptamer 70.15
AGCTCGAGCTCGAATTCCCTACGAACCCAGGAGATAAGGGGGAAAACTCTGGAAAACGGGCCCGGATCCGTC

SEQ ID NO: 4
Aptamer 70.28
AGCTCGAGCTCGAATTCACAAGAACCGGACCGGGTGAGAACCGAGACAAACACCCACCAAGAGGGCCCGGATCCGTC

SEQ ID NO: 5
Aptamer 70.28t34
AGCTCGAGCTCGAATTCGGGAACCGGACGGGTGAGAACCGAGACAAACACCGGGCCCGGATCCGTC

SEQ ID NO: 6
Aptamer 80.55,65
AGCTCGAGCTCGAATTCATTTAATTCCATAATGGCTCACCACAAGGGGAACGTTGATGAAATAGGGCCCGGATCCGTC

SEQ ID NO: 7
5' flanking sequence of the exemplified aptamers
AGCTCGAGCTCGAATTC

SEQ ID NO: 8
3' flanking sequence of the exemplified aptamers, from 5' end of self cleaving ribozyme
GGGCCCGGATCCGTC SEQ ID NO: 9
upstream primer T3-Start
AATTAACCCTCACTAAAGGGTAGACAATTCACTGC SEQ ID NO: 10
downstream primer pcDNA3.1END
GCATGCCTGCTATTGTCTTCCC

What is claimed is:

1. An RNA oligonucleotide comprising an aptamer flanked by two self-cleaving ribozymes, wherein the aptamer comprises the sequence set forth in SEQ ID NO:2, SEQ ID NO:3 or SEQ ID NO:6.

2. An RNA oligonucleotide comprising an aptamer flanked by two self-cleaving ribozymes, wherein the self-cleaving ribozymes comprise SEQ ID NO:9 or SEQ ID NO:10.

3. The RNA oligonucleotide of claim 2, further comprising a third ribozyme between the two self-cleaving ribozymes and adjacent to the aptamer, wherein the third ribozyme is not self-cleaving.

4. A vector encoding the RNA oligonucleotide of claim 2, wherein the vector further comprises a promoter directing transcription of the RNA oligonucleotide.

5. The vector of claim 4, wherein the vector is a retroviral vector.

6. The vector of claim 4, wherein the vector is a pBabe MuLV retroviral vector and the promoter is a tRNA$^{val}$ promoter.

7. The vector of claim 4, further comprising a viral long terminal repeat (LTR) driving expression of the vector, wherein the aptamer is in reverse orientation to the LTR, and wherein the vector is an MMP-eGFP vector.

8. A cell transfected with the vector of claim 4.

9. The cell of claim 8, wherein the cell is a mammalian cell.

10. The cell of claim 8, wherein the cell is a human cell.

11. The cell of claim 8, wherein the aptamer is capable of inhibiting replication of a virus in the cell.

12. The cell of claim 11, wherein the cell is infected with the virus.

13. The cell of claim 11, wherein the virus is a retrovirus.

14. The cell of claim 11, wherein the virus is HIV-1.

15. A cell expressing an aptamer, wherein the aptamer does not comprise flanking sequences that interfere with the aptamer function, wherein the aptamer binds to a component of a retrovirus, and wherein the aptamer comprises the sequence set forth in SEQ ID NO:2, SEQ ID NO:3 or SEQ ID NO:6 and/or the aptamer is cleaved from an RNA oligonucleotide comprising an RNA sequence flanked by two self-cleaving ribozymes that comprise SEQ ID NO:9 or SEQ ID NO:10.

16. The cell of claim 15, wherein the cell is infected with HIV-1 virus.

17. The cell of claim 15, wherein the aptamer inhibits replication of HIV-1 virus when the aptamer and the virus are present in the cell.

18. The RNA oligonucleotide of claim 2, wherein the ribozymes recognize a GUC cleavage motif adjacent to the aptamer.

19. The cell of claim 17, wherein the ribozymes recognize a GUC cleavage motif adjacent to the aptamer.

20. The RNA oligonucleotide of claim 1, further comprising a third ribozyme between the two self-cleaving ribozymes and adjacent to the aptamer, wherein the third ribozyme is not self-cleaving.

21. A vector encoding the RNA oligonucleotide of claim 1, wherein the vector further comprises a promoter directing transcription of the RNA oligonucleotide.

22. The vector of claim 21, wherein the vector is a retroviral vector.

23. The vector of claim 21, wherein the vector is a pBabe MuLV retroviral vector and the promoter is a tRNA$^{val}$ promoter.

24. The vector of claim 21, further comprising a viral long terminal repeat (LTR) driving expression of the vector, wherein the aptamer is in reverse orientation to the LTR, and wherein the vector is an MMP-eGFP vector.

25. A cell transfected with the vector of claim 21.

26. The cell of claim 25, wherein the aptamer is capable of inhibiting replication of a virus in the cell.

27. The cell of claim 25, wherein the cell is infected with the virus.

28. The cell of claim 27, wherein the virus is a retrovirus.

29. The cell of claim 28, wherein the virus is HIV-1.

30. The cell of claim 25, wherein the cell is a mammalian cell.

31. The cell of claim 25, wherein the cell is a human cell.

32. The RNA oligonucleotide of claim 1, wherein the ribozymes recognize a GUC cleavage motif adjacent to the aptamer.

* * * * *

UNITED STATES PATENT AND TRADEMARK OFFICE
CERTIFICATE OF CORRECTION

| | | |
|---|---|---|
| PATENT NO. | : 7,700,759 B2 | Page 1 of 1 |
| APPLICATION NO. | : 10/999686 | |
| DATED | : April 20, 2010 | |
| INVENTOR(S) | : Vinayaka R. Prasad and Pheroze Joshi | |

It is certified that error appears in the above-identified patent and that said Letters Patent is hereby corrected as shown below:

Column 1, lines 15-22, should read:

-- STATEMENT OF GOVERNMENT SUPPORT

This invention was made with government support under grant number AI061797 awarded by the National Institutes of Health. The government has certain rights in the invention. --

Signed and Sealed this
Twenty-fourth Day of November, 2015

Michelle K. Lee
*Director of the United States Patent and Trademark Office*